(12) United States Patent
Zygorodimos

(10) Patent No.: US 12,172,002 B2
(45) Date of Patent: Dec. 24, 2024

(54) REAL-TIME ESTIMATION OF ELECTRODE ARRAY POSE DURING INTRA-COCHLEAR INSERTION

(71) Applicant: Cochlear Limited, Macquarie University (AU)

(72) Inventor: Matthew Zygorodimos, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 353 days.

(21) Appl. No.: 17/299,264

(22) PCT Filed: Aug. 10, 2020

(86) PCT No.: PCT/IB2020/057525
§ 371 (c)(1),
(2) Date: Jun. 2, 2021

(87) PCT Pub. No.: WO2021/028824
PCT Pub. Date: Feb. 18, 2021

(65) Prior Publication Data
US 2022/0023618 A1    Jan. 27, 2022

Related U.S. Application Data

(60) Provisional application No. 62/885,449, filed on Aug. 12, 2019.

(51) Int. Cl.
*A61N 1/05* (2006.01)
*A61N 1/36* (2006.01)
*A61N 1/372* (2006.01)

(52) U.S. Cl.
CPC ....... *A61N 1/0541* (2013.01); *A61N 1/36039* (2017.08); *A61N 1/37282* (2013.01)

(58) Field of Classification Search
None
See application file for complete search history.

(56) References Cited

U.S. PATENT DOCUMENTS

| | | | |
|---|---|---|---|
| 6,636,768 | B1 | 10/2003 | Harrison |
| 8,886,330 | B2 | 11/2014 | Taylor et al. |

(Continued)

FOREIGN PATENT DOCUMENTS

| | | |
|---|---|---|
| WO | WO 03/030738 | 4/2003 |
| WO | WO 2016/035027 | 3/2016 |

(Continued)

OTHER PUBLICATIONS

Campbell et al., "Cochlear response telemetry: intracochlear electrocochleography via cochlear implant neural response telemetry pilot study results," Otol. Neurotol., vol. 36(3), pp. 399-405 (2015).

(Continued)

*Primary Examiner* — Erica S Lee
(74) *Attorney, Agent, or Firm* — Knobbe, Martens, Olson & Bear, LLP

(57) ABSTRACT

A method includes receiving first information regarding a pose of a structure in a first time period. The structure is configured to be inserted into a body portion of a recipient. The first information includes at least one of: a first estimate of the pose of the structure in the first time period, and a first measurement set including one or more first measurement values. At least some of the one or more first measurement values are generated using a plurality of sensors distributed along the structure. The one or more first measurement values are indicative of the pose of the structure in the first time period. The method further includes generating a (Continued)

second estimate of the pose of the structure using at least the first information and a probabilistic model of the structure and/or the body portion.

31 Claims, 15 Drawing Sheets

(56) References Cited

U.S. PATENT DOCUMENTS

| | | | |
|---|---|---|---|
| 9,107,621 | B2 | 8/2015 | Grasso et al. |
| 9,173,585 | B2 | 11/2015 | Tsampazis et al. |
| 9,597,503 | B2 | 3/2017 | Risi et al. |
| 9,987,490 | B2 | 6/2018 | Kabot et al. |
| 10,898,286 | B2 * | 1/2021 | Srinivasan ............ A61B 34/20 |
| 11,503,986 | B2 * | 11/2022 | Ye ....................... A61B 5/7285 |
| 2006/0155346 | A1 | 7/2006 | Miller |
| 2011/0066160 | A1 | 3/2011 | Simaan et al. |
| 2015/0112408 | A1 * | 4/2015 | Kals ................... A61N 1/0541 607/57 |
| 2015/0314122 | A1 | 11/2015 | Kabot et al. |
| 2016/0059015 | A1 | 3/2016 | Risi et al. |
| 2017/0014194 | A1 | 1/2017 | Duindam et al. |
| 2018/0140829 | A1 | 5/2018 | Ramos de Miguel, Sr. et al. |
| 2018/0280687 | A1 * | 10/2018 | Carter ..................... A61N 1/08 |

FOREIGN PATENT DOCUMENTS

| | | |
|---|---|---|
| WO | WO 2017/221193 | 12/2017 |
| WO | WO 2018/200450 | 11/2018 |

OTHER PUBLICATIONS

Degen, Chantal, M.D. "Effect of Electrode Position on Electrophysiological and Psychophysical Parameters in CI Patients with Lateral and Perimodiolar Electrode Arrays," presentation at CI 2017 Pediatric 15th Symposium on Cochlear Implants in Children, 18 pages (2017).

International Search Report and Written Opinion for PCT/IB2020/057525 mailed on Nov. 11, 2020 in 14 pgs.

Extended European search report for EP 20852215.1 mailed on Aug. 2, 2023 in 7 pages.

* cited by examiner

REAL-TIME ESTIMATION OF ELECTRODE ARRAY POSE DURING INTRA-COCHLEAR INSERTION

BACKGROUND

Field

The present application relates generally to systems and methods for monitoring the implantation of medical devices within the body of a recipient, and more specifically, to facilitating positioning of stimulation elements of a cochlear-implanted auditory prosthesis during implantation.

Description of the Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As a result, individuals suffering from conductive hearing loss might receive an auditory prosthesis that generates mechanical motion of the cochlea fluid instead of a hearing aid based on the type of conductive loss, amount of hearing loss and customer preference. Such prostheses include, for example, bone conduction devices and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

SUMMARY

In one aspect disclosed herein, a method comprises receiving first information regarding a pose of a structure in a first time period. The structure is configured to be inserted into a body portion of a recipient. The first information comprises at least one of: a first estimate of the pose of the structure in the first time period, and a first measurement set comprising one or more first measurement values. At least some of the one or more first measurement values are generated using a plurality of sensors distributed along the structure. The one or more first measurement values are indicative of the pose of the structure in the first time period. The method further comprises generating a second estimate of the pose of the structure using at least the first information and a probabilistic model of the structure and/or the body portion.

In another aspect disclosed herein, a method comprises accessing information characterizing states and transitions between states of a structure at least partially inserted into a body portion of a recipient. The method further comprises accessing expectation measurement values or ranges of values expected to be generated by at least one sensor of the structure. The method further comprises obtaining at least one first measurement value from the at least one sensor at a first time period. The method further comprises determining, in response to a comparison of the at least one first measurement value to the expectation measurement values or ranges of values, a first state of the structure during the first time period.

In still another aspect disclosed herein, a system comprises at least one data input interface configured to receive data from a plurality of transducers during implantation of a medical device on or in a recipient. The system further comprises at least one controller in operative communication with the at least one data input interface. The at least one controller is configured to access a probabilistic model of a parameterized description of a pose of the medical device relative to the body portion and to generate an estimate of a current pose of the medical device in response at least in part to the data and the probabilistic model. The system further comprises at least one output interface in operative communication with the at least one controller. The at least one output interface is configured to provide information regarding the estimated pose of the medical device.

In still another aspect disclosed herein, a non-transitory computer readable storage medium has stored thereon a computer program that instructs a computer system to provide real-time information regarding a structure as the structure is being inserted into and/or retracted from a region. The computer system provides the real-time information by at least receiving information regarding the structure while the structure is being inserted into the region, accessing a parameterized description of the structure and/or the region, and using at least one processor to generate, based on the information and the parameterized description, an estimated pose of the structure relative to the region.

BRIEF DESCRIPTION OF THE DRAWINGS

Embodiments are described herein in conjunction with the accompanying drawings, in which.

DETAILED DESCRIPTION

Certain embodiments described herein provide a system and method for providing medical professionals (e.g., surgeons) with real-time information (e.g., feedback) regarding the pose of a structure (e.g., electrode array of a cochlear implant system) as the structure is being implanted into a body portion (e.g., cochlea) of a recipient. Such real-time information can be advantageously used to avoid suboptimal implantation of the structure, to provide better and more consistent outcomes for recipients, and/or to improve the surgical techniques of the medical professionals.

Certain embodiments described herein utilize measurements made during the implantation and a probabilistic model of the structure and/or the body portion to estimate the pose of the structure relative to the body portion. For example, the system and method can provide a mapping of the progress of an electrode array as the array is being inserted into the cochlea by: making measurements during the insertion that relate to the pose of the array relative to the cochlea, using the resulting measurement values with the probabilistic model to estimate the pose, or the change of pose, of the electrode array in the cochlea, and providing feedback information regarding the estimates in real-time to the operator (e.g., via the auditory prosthesis system or an auxiliary device). Metrics regarding the pose of the electrode array (e.g., angular depth; extend of foldover; speed of insertion; distance from basilar membrane; deflection within the canals) can be reported continuously to the operator. Events related to the insertion of the electrode array (e.g., a snagged electrode beginning to fold; a scala dislocation) can be detected and used to trigger a distinct alert to the operator.

Figure 1:
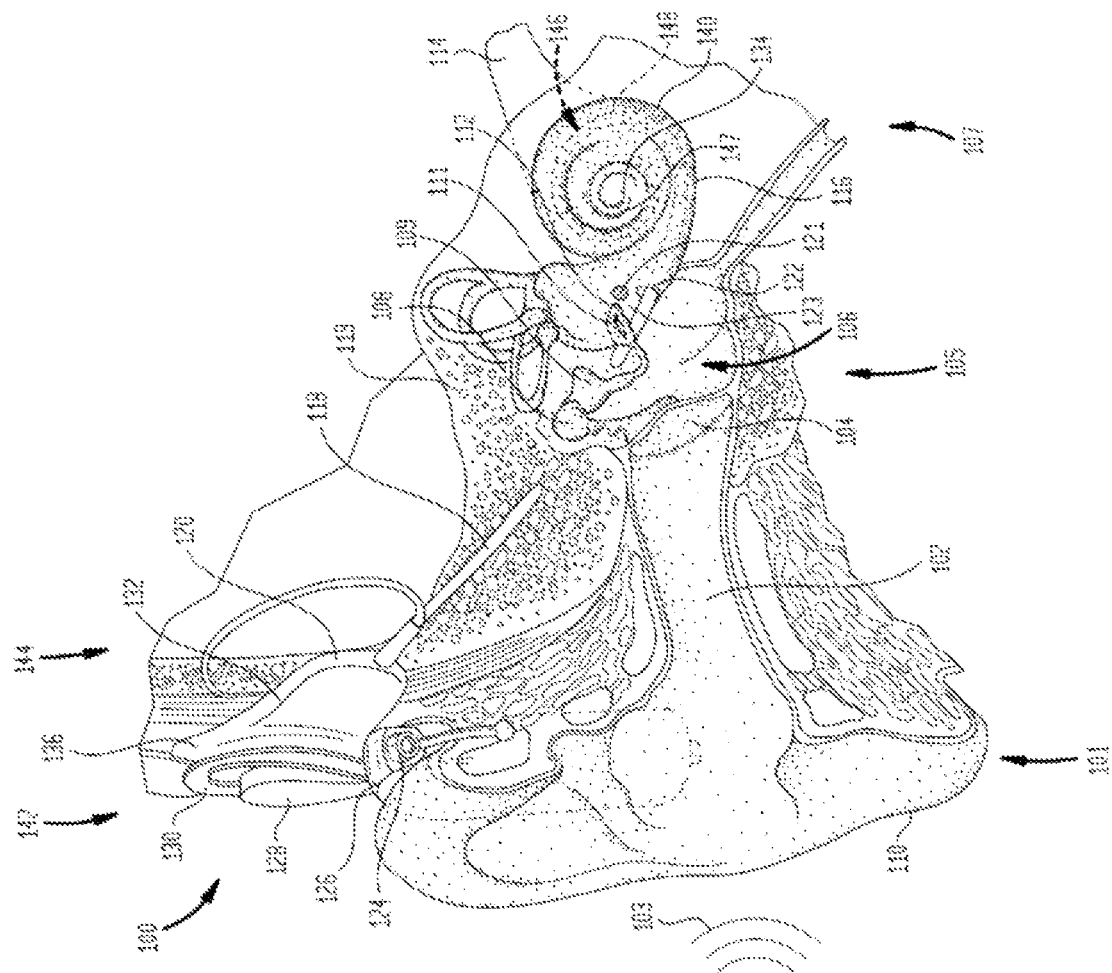
FIG. 1 is a perspective view of an example auditory prosthesis implanted in a recipient with a stimulation assembly inserted into the cochlea in accordance with certain embodiments described herein.

FIG. 1 is a perspective view of an example auditory prosthesis 100 (e.g., cochlear implant), implanted in a recipient with a stimulation assembly 118 inserted into the cochlea 140 in accordance with certain embodiments described herein. As shown in FIG. 1, the recipient has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within the cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, the example auditory prosthesis 100 comprises one or more components which are temporarily or permanently implanted in the recipient. The example auditory prosthesis 100 is shown in FIG. 1 with an external component 142 which is directly or indirectly attached to the recipient's body, and an internal component 144 which is temporarily or permanently implanted in the recipient (e.g., positioned in a recess of the temporal bone adjacent to the auricle 110 of the recipient). The external component 142 typically comprises one or more sound input elements (e.g., an external microphone 124) for detecting sound, a sound processing unit 126 (e.g., disposed in a Behind-The-Ear unit), a power source (not shown), and an external transmitter unit 128. In the illustrative embodiments of FIG. 1, the external transmitter unit 128 comprises an external coil 130 (e.g., a wire antenna coil comprising multiple turns of electrically insulated single-strand or multi-strand platinum or gold wire) and, preferably, a magnet (not shown) secured directly or indirectly to the external coil 130. The external coil 130 of the external transmitter unit 128 is part of an inductive radio frequency (RF) communication link with the internal component 144. The sound processing unit 126 processes the output of the microphone 124 that is positioned externally to the recipient's body, in the depicted embodiment, by the recipient's auricle 110. The sound processing unit 126 generates encoded signals, sometimes referred to herein as encoded data signals, which are provided to the external transmitter unit 128 (e.g., via a cable).

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate stimulation assembly 118. In some embodiments, the internal receiver unit 132 and the stimulator unit 120 are hermetically sealed within a biocompatible housing, sometimes collectively referred to as a stimulator/receiver unit. The internal receiver unit 132 comprises an internal coil 136 (e.g., a wire antenna coil comprising multiple turns of electrically insulated single-strand or multi-strand platinum or gold wire), and preferably, a magnet (also not shown) fixed relative to the internal coil 136. The internal coil 136 receives power and/or data signals from the external coil 130 via a transcutaneous energy transfer link (e.g., an inductive RF link). The stimulator unit 120 generates electrical stimulation signals based on the data signals, and the stimulation signals are delivered to the recipient via the elongate stimulation assembly 118.

The elongate stimulation assembly 118 has a proximal end connected to the stimulator unit 120, and a distal end implanted in the cochlea 140. The stimulation assembly 118 extends from the stimulator unit 120 to the cochlea 140 through the mastoid bone 119. In some embodiments, the stimulation assembly 118 may be implanted at least in the basal region 116, and sometimes further. For example, the stimulation assembly 118 may extend towards the apical end of the cochlea 140, referred to as the cochlea apex 134. In certain circumstances, the stimulation assembly 118 may be inserted into the cochlea 140 via a cochleostomy 122. In other circumstances, a cochleostomy 122 may be formed through the round window 121, the oval window 112, the promontory 123, or through an apical turn 147 of the cochlea 140.

The elongate stimulation assembly 118 comprises a longitudinally aligned and distally extending array 146 (e.g., electrode array; contact array) of stimulation elements 148 (e.g., electrical electrodes; electrical contacts; optical emitters; optical contacts). The stimulation elements 148 are longitudinally spaced from one another along a length of the elongate body of the stimulation assembly 118. For example, the stimulating assembly 118 can comprise an array 146 comprising twenty-two (22) stimulation elements 148 that are configured to deliver stimulation to the cochlea 140. Although the array 146 of stimulation elements 148 can be disposed on the stimulation assembly 118, in most practical applications, the array 146 is integrated into the stimulation assembly 118 (e.g., the stimulation elements 148 of the array 146 are disposed in the stimulation assembly 118). As noted, the stimulator unit 120 generates stimulation signals (e.g., electrical signals; optical signals) which are applied by the stimulation elements 148 to the cochlea 140, thereby stimulating the auditory nerve 114.

A variety of types of intra-cochlear stimulation assemblies 118 are compatible with certain embodiments described herein, including but not limited to: short, straight, and perimodiolar. A perimodiolar stimulation assembly 118 is configured to adopt a curved configuration during and/or after implantation into the cochlea 140. To achieve this, in certain embodiments, the perimodiolar stimulation assembly 118 is pre-curved to the same general curvature of the cochlea 140. Such examples of the stimulation assembly 118 can be held straight by, for example, a stiffening stylet (not shown) or sheath which is removed during implantation, or alternatively varying material combinations or the use of shape memory materials, so that the stimulation assembly 118 may adopt its curved configuration when in the cochlea 140. Other methods of implantation, as well as other stimulation assemblies 118 which adopt a curved configuration, may be used. The stimulation assembly 118 of certain other embodiments comprises a non-perimodiolar stimulation assembly 118. For example, the stimulation assembly 118 can comprise a straight stimulation assembly 118 or a mid-scala assembly which assumes a mid-scala position during or following implantation. Alternatively, the stimulation assembly 118 can comprise a short electrode implanted into at least the basal region of the cochlea 140.

Figure 2:
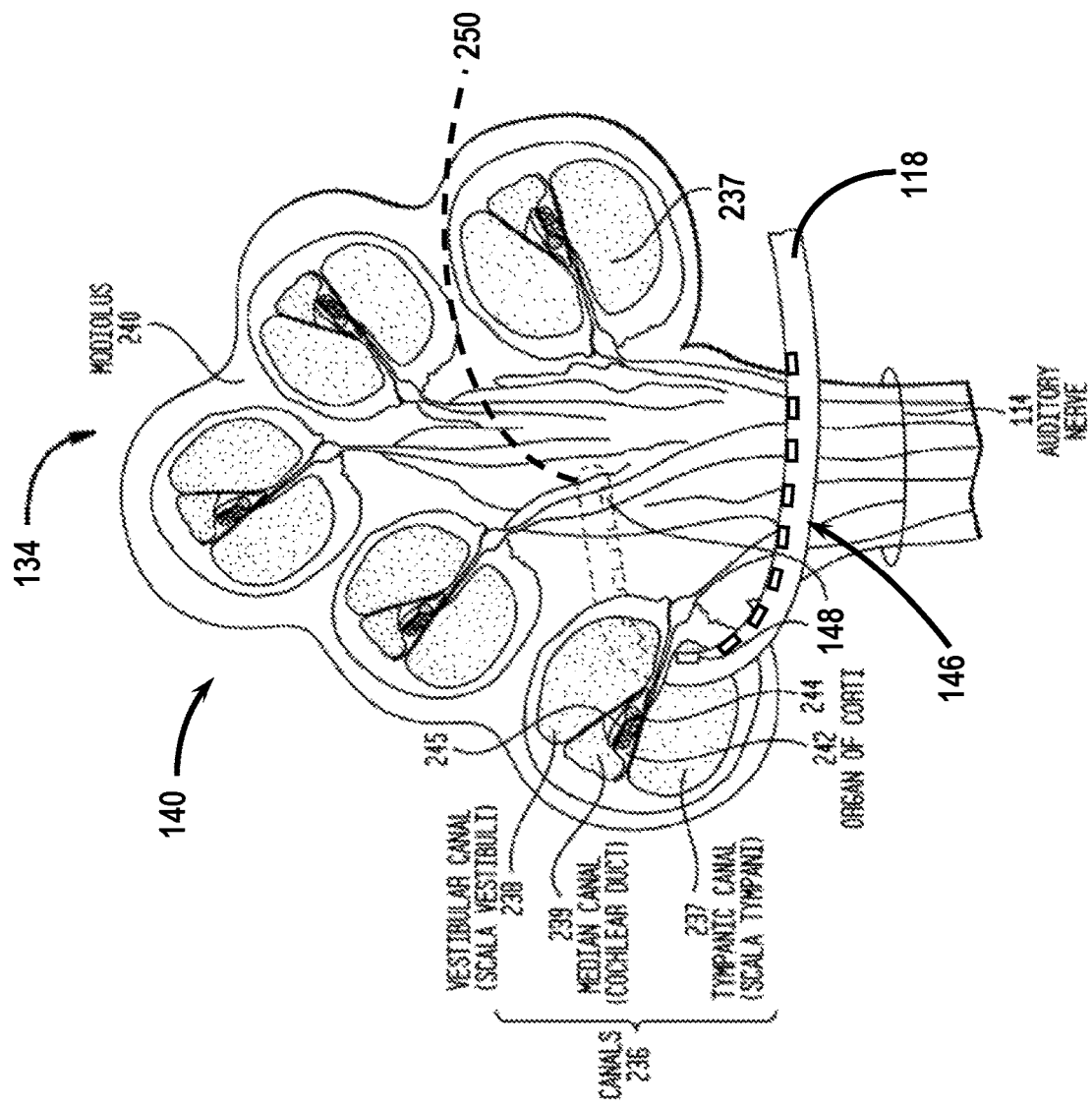
FIG. 2 is cross-sectional view of the cochlea illustrating the stimulating assembly partially implanted therein in accordance with certain embodiments described herein.

FIG. 2 is cross-sectional view of the cochlea 140 illustrating the stimulating assembly 118 partially implanted therein in accordance with certain embodiments described herein. Only a subset of the stimulation elements 148 of the stimulation assembly 118 is shown in FIG. 2. The cochlea 140 is a conical spiral structure that comprises three parallel fluid-filled canals or ducts, collectively and generally referred to herein as canals 236. Canals 236 comprise the tympanic canal 237, also referred to as the scala tympani 237, the vestibular canal 238, also referred to as the scala vestibuli 238, and the median canal 239, also referred to as the scala media 239. The cochlea 140 includes the modiolus 240 which is a conical shaped central region around which the cochlea canals 236 spiral. The modiolus 240 consists of spongy bone in which the cochlea nerve cells, sometimes referred to herein as the spiral ganglion cells, are situated. The cochlea canals 236 generally turn 2.5 times around the modiolus 240.

In normal hearing, sound entering the auricle 110 (see, e.g., FIG. 1) causes pressure changes in the cochlea 140 that travel through the fluid-filled tympanic and vestibular canals 237, 238. The organ of Corti 242, which is situated on the basilar membrane 244 in scala media 239, contains rows of hair cells (not shown) which protrude from its surface. Located above the hair cells is the tectoral membrane 245 which moves in response to pressure variations in the fluid-filled tympanic and vestibular canals 237, 238. Small relative movements of the layers of the tectoral membrane 245 are sufficient to cause the hair cells to move, thereby causing the creation of a voltage pulse or action potential which travels along the associated nerve fibers that connect the hair cells with the auditory nerve 114. The auditory nerve 114 relays the impulses to the auditory areas of the brain (not shown) for processing.

Typically, in cochlear implant recipients, some portion of the cochlea 140 (e.g., the hair cells) is damaged such that the cochlea 140 cannot transduce pressure changes into nerve impulses for relay to the brain. As such, the stimulating elements 148 of the stimulating assembly 118 are used to directly stimulate the cells to create nerve impulses resulting in perception of a received sound (e.g., to evoke a hearing precept).

To insert the intra-cochlear stimulating assembly 118 into the cochlea 140, an opening (facial recess) is created through the recipient's mastoid bone 119 (see, e.g., FIG. 1) to access the recipient's middle ear cavity 106 (see, e.g., FIG. 1). An opening is then created from the middle ear 106 into the cochlea 140 through, for example, the round window 121, oval window 112, the promontory 123, etc. of the cochlea 140. The stimulating assembly 118 is then gently advanced (e.g., pushed) forward into the cochlea 140 until the stimulating assembly 118 achieves the implanted position. As shown in FIGS. 1 and 2, the stimulating assembly 118 follows the helical shape of the cochlea 140. That is, the stimulating assembly 118 spirals around the modiolus 240.

The effectiveness of the stimulation by the stimulation assembly 118 depends, at least in part, on the place along the basilar membrane 244 where the stimulation is delivered. That is, the cochlea 140 has characteristically been referred to as being "tonotopically mapped," in that regions of the cochlea 140 toward the basal end are more responsive to high frequency signals, while regions of cochlea 140 toward the apical end are more responsive to low frequency signals. These tonotopical properties of the cochlea 140 are exploited in a cochlear implant by delivering stimulation within a predetermined frequency range to a region of the cochlea 140 that is most sensitive to that particular frequency range. However, this stimulation relies on the particular stimulation elements 148 having a final implanted positioned adjacent to a corresponding tonotopic region of the cochlea 140 (e.g., a region of the cochlea 140 that is sensitive to the frequency of sound represented by the stimulation element 148).

To achieve a selected final implanted position, the apical (e.g., distal end/tip) portion 250 of the array 146 is placed at a selected angular position (e.g., angular insertion depth). As used herein, the angular position or angular insertion depth refers to the angular rotation of the apical portion 250 of the array 146 from the cochleostomy 122 (e.g., round window 121) through which the stimulation assembly 118 enters the cochlea 140. As such, the angular position/angular insertion depth may be expressed in terms of how many angular degrees the apical portion 250 has traveled within the cochlea 140 with respect to the cochleostomy 122. For example, an angular insertion depth of one hundred and eighty (180) degrees indicates that the apical portion 250 has traveled around half (½) of the first turn of the cochlea 140. An angular insertion depth of three hundred and sixty (360) degrees indicates that the apical portion 250 has traveled completely around the first turn of the cochlea 140.

In certain embodiments, while the stimulation assembly 118 is being implanted (e.g., during a surgical procedure conducted by an operator, such as a medical professional, surgeon, and/or an automated or robotic surgical system), a location and/or an orientation of the array 146 relative to the cochlea 140 (e.g., collectively referred to as the pose of the array 146) is adjusted as the array 146 is advanced and placed into position within the cochlea 140. The goal of the implantation is that the fully-implanted array 146 has an optimal pose in which the array 146 is positioned such that the stimulation elements 148 are adjacent to the corresponding tonotopic regions of the cochlea 140. To achieve the optimal pose, the array 146 is expected to follow a trajectory in the cochlea 140 whereby (i) the stimulation elements 148 are distributed linearly along an axis of the cochlear duct 239, (ii) the array 146 does not make contact with the basilar membrane 244, and (iii) the stimulation elements 148 are in close proximity to the modiolar wall (e.g., if the array 146 is pre-curved) or the stimulation elements 148 are distant from the modiolar wall (e.g., if the array 146 is not pre-curved).

However, one or more these expectations may be violated during insertion of the array 146. For example, the apical portion 250 of the array 146 can become snagged on the wall of the cochlear duct 239, the array 146 can become buckled, folded, and/or overinserted, and/or portions of the cochlea 140 (e.g., scala tympani 237; scala vestibuli 238; cochlear duct 239; organ of Corti 242; basilar membrane 244) can be dislocated, resulting in sub-optimal placement of the array 146. It is desirable to provide the operator with information regarding the pose and/or state of the array 146 during the implantation process (e.g., feedback information provided in real-time). For example, during the implantation process, metrics related to the pose of the array 146 (e.g., angular depth; extend of foldover; speed of insertion; distance from basilar membrane 244; deflection within the canals 236) can be reported continuously, at predetermined intervals, and/or in response to requests by the operator, and alerts regarding events related to insertion (e.g., snagged electrode; scala dislocation; other non-optimal conditions) can be provided to the operator, so the operator can take corrective measures.

Figure 3:
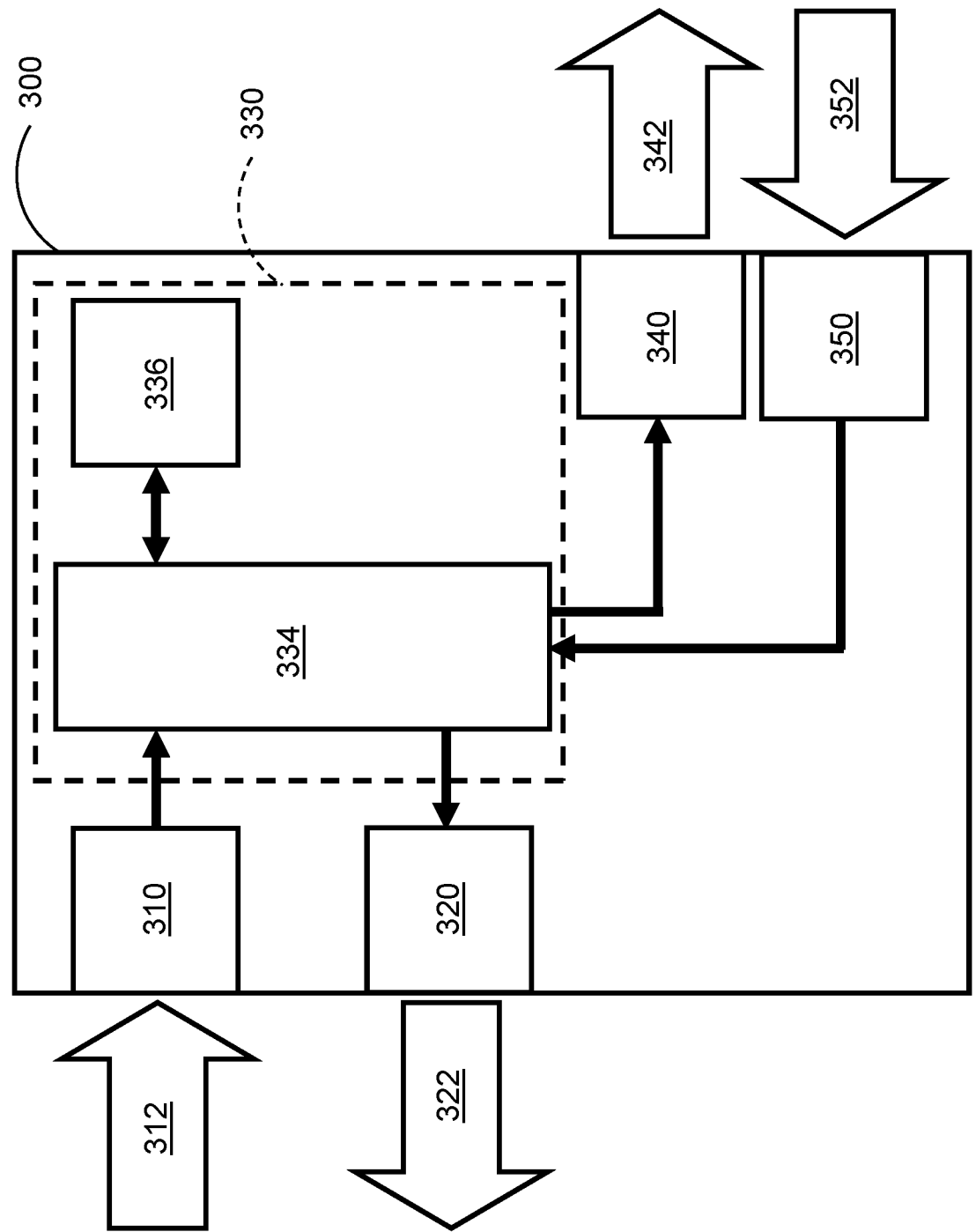
FIG. 3 schematically illustrates an example system in accordance with certain embodiments described herein.

FIG. 3 schematically illustrates an example system 300 in accordance with certain embodiments described herein. The system 300 comprises at least one data input interface 310 configured to receive data 312 from a plurality of transducers during implantation of a medical device on or in a body portion of a recipient. The system 300 further comprises at least one control output interface 320 configured to transmit control signals 322 to the plurality of transducers. The plurality of transducers is responsive to the control signals 322 by generating the data 312. The system 300 further comprises at least one controller 330 in operative communication with the at least one data input interface 310 and the at least one control output interface 320. The at least one controller 330 is configured to access a probabilistic model of a parameterized description of a pose of the medical device relative to the body portion. The at least one controller 330 is further configured to generate an estimate of a current pose of the medical device in response at least in part to the received data 312 and the probabilistic model. The system 300 further comprises at least one output interface 340 in operative communication with the at least one controller 330 and configured to provide information 342 regarding the estimated pose of the medical device. In certain embodiments, the system 300 further comprises at least one user input interface 350 in operative communication with the at least one controller 330 and configured to provide user input 352 to the at least one controller 330.

In certain embodiments, the system 300 comprises at least one computing device configured to be in operative communication with the plurality of transducers (e.g., via the at least one data input interface 310 and the at least one control output interface 320) and in operative communication (e.g., via the at least one output interface 340 and the at least one user input interface 350) with an operator (e.g., medical professional; surgeon; automated or robotic surgical system). The at least one computing device can include, but is not limited to: a desktop computer, a laptop computer, a mobile computing device or accessory; a smartphone; a smart tablet. The at least one computing device can be in communication with another computing device (e.g., via the at least one output interface 340 and/or the at least one user input interface 350) that is being utilized by the operator (e.g., an external device being used by a medical professional or surgeon; a component of the automated or robotic surgical system). In certain embodiments, the at least one computing device is external to the implantable medical device, while in certain other embodiments, the at least one computing device is incorporated in the implantable medical device.

The at least one data input interface 310, the at least one control output interface 320, the at least one output interface 340, and/or the at least one user input interface 350 can comprise any combination of wired and/or wireless ports, including but not limited to: Universal Serial Bus (USB) ports; Institute of Electrical and Electronics Engineers (IEEE) 1394 ports; PS/2 ports; network ports; Ethernet ports; Bluetooth ports; wireless network interfaces. In certain embodiments, the at least one data input interface 310 and the at least one control output interface 320 are integral with one another (e.g., comprising the same ports as one another), while in certain other embodiments, the at least one data input interface 310 and the at least one control output interface 320 are separate from one another. In certain embodiments, the at least one data input interface 310 and the at least one control output interface 320 are in operative communication with the same transducers as one another, while in certain other embodiments, the at least one data input interface 310 and the at least one control output interface 320 are in operative communication with different transducers as one another.

The at least one output interface 340 of certain embodiments is configured to be in operative communication with at least one communication device (e.g., display device; screen; status indicator light; audio device; speaker; vibration motor) configured to communicate information to the operator during the implantation of the medical device. For example, the at least one communication device can provide information, alerts, and/or alarms to the operator regarding the pose of the medical device and/or regarding the operative status of the system 300. The at least one user input interface 350 can be configured to be in operative communication with one or more keyboard, computer mouse, touchscreen, switches, buttons, or other devices with which a human operator (e.g., medical professional; surgeon) can provide the system 300 with commands or data.

In certain embodiments, the at least one controller 330 is configured to transmit the control signals 322 to the plurality of transducers automatically (e.g., at a predetermined constant repetition rate; at times determined by the internal logic of the controller 330) during the implantation of the medical device. For example, the plurality of transducers can be activated or triggered to perform data collection automatically upon connection of the system 300 to the plurality of transducers of the medical device (e.g., connection of a surgical sound processing unit 126 to a cochlear implant system 100 during implantation). In certain other embodiments, the at least one controller 330 is configured to receive triggering signals from the at least one user input interface 350 intermittently during the implantation of the medical device. The at least one controller 330 can be configured to respond to the triggering signals by transmitting the control signals 322 to the plurality of transducers. In this way, the plurality of transducers can be selectively activated by the human operator (e.g., by pressing a button of an external device in operative communication with the at least one user input interface 350) and/or the automated or robotic surgical system. In certain other embodiments, the controller 300 does not send control signals 322 to the plurality of transducers and the system 300 does not comprise a control output interface 320.

In certain embodiments, the at least one controller 330 comprises at least one processor 334 and at least one storage device 336 in operative communication with the at least one processor 334. The at least one storage device 336 can be configured to collect and store the data 312 received from the plurality of transducers, and the at least one processor 334 can be configured to generate the estimate of the pose of the medical device in response at least in part to the stored data. The at least one processor 334 can comprise a microprocessor or microcontroller configured to receive data 312 via the at least one data input interface 310 and to transmit the received data 312 to the at least one storage device 336. The at least one processor 334 can also be configured to access the data 312 (e.g., stored on the at least one storage device 336), to access the probabilistic model of a parameterized description of a pose of the medical device (e.g., stored on the at least one storage device 336), to execute instructions (e.g., stored on the at least one storage device 336), and to generate and provide information (e.g., regarding the estimated pose of the medical device) to the at least one output interface 340 and/or to the at least one storage device 336 to be stored and later retrieved.

In certain embodiments, the at least one processor 334 is configured to filter the data 312 received from the plurality of transducers. For example, the at least one processor 334 can filter (e.g., in the time domain; using a median filter; using an exponentially weighted moving average filter) the data 312 generated by multiple measurements. For another example, the at least one processor 334 can apply more weighting to more recently generated data 312 (e.g., to selectively apply more weighting to data 312 potentially affected by the presence of the electrode 148 in the cochlea 140). In certain embodiments, the at least one processor 334 is configured to aggregate the data 312 generated by a transducer (e.g., aggregating the last 10 measurements by a transducer). In certain embodiments, the at least one processor 334 is configured to aggregate the data 312 generated by multiple transducers (e.g., aggregating the last 10 measurements by transducers when each of the transducers is at a predetermined location relative to the body portion in which the medical device is being implanted, such as 5 mm from the round window 121 of the cochlea 140).

In certain embodiments, the at least one processor 334 is configured to associate the data 312 to particular transducers (e.g., electrode contacts; microphones) based on prior knowledge of the configuration of transducers (e.g., electrode montage) used for measurement collection. For example, data 312 can be associated to a position of an electrode 148 in the cochlea 140 using a prior estimate of the pose of the electrode array 146. In certain embodiments, the at least one processor 334 is configured to extrapolate the data 312 to nearby locations using interpolation (e.g., inverse distance weighted; piecewise linear interpolation).

The at least one storage device 336 can comprise at least one tangible (e.g., non-transitory) computer readable storage medium, examples of which include but are not limited to: read only memory (ROM); random access memory (RAM); magnetic disk storage media; optical storage media; flash memory. The at least one storage device 336 can be encoded with software (e.g., a computer program downloaded as an application) comprising computer executable instructions for instructing a computer system (e.g., measurement logic and/or evaluation logic to be executed by the at least one processor 334). For example, the measurement logic can be executed by the at least one processor 334 to generate the control signals 322 that activate and/or otherwise control the plurality of transducers. For another example, the evaluation logic can be executed by the at least one processor 334 to evaluate the data 312 received from the plurality of transducers, to generate estimates of the pose of the medical device using the probabilistic model, and to provide the information 342 regarding the estimated pose of the medical device.

In certain embodiments, implantation of the medical device comprises insertion of at least a portion of the medical device into a body portion of the recipient. For example, the medical device can comprise a stimulation assembly 118 of a cochlear implant auditory prosthesis 100 and the body portion can comprise a cochlea 140 of the recipient.

In certain embodiments, at least some of the transducers are configured to be used as stimulators to initiate a biophysical phenomenon dependent on the current pose of the medical device, and at least some of the transducers are configured to be used as sensors to generate the data 312 indicative of the biophysical phenomenon. In certain such embodiments, at least some of the transducers are configured to be used as both stimulators and as sensors.

In certain embodiments, the medical device comprises at least some of the plurality of transducers. For example, the plurality of transducers can comprise the stimulation elements 148 (e.g., electrodes) of the electrode array 146 of the stimulation assembly 118 of the cochlear implant auditory prosthesis 100 (e.g., to generate transimpedance data in which the electrodes 148 are configured to be used as both stimulators and as sensors). In certain other embodiments, the plurality of transducers comprises at least one transducer that is not part of the medical device. For example, to provide electrocochleography (e.g., cochlear microphonic) data, the plurality of transducers can comprise the electrodes 148 of the electrode array 146 (which are part of the stimulation assembly 118 and which are configured to be used as sensors), and one or more actuators which are not part of the stimulation assembly 118 (and which are configured to be used as stimulators). The one or more actuators can be either implanted or external (e.g., in the ear canal 102) and can include, but are not limited to, acoustic receivers, bone conduction devices, middle-ear/stapes/round window oscillators, either implanted or external (e.g., in the ear canal 102). For another example, to provide stapedius reflex data, the plurality of transducers can comprise the electrodes 148 of the electrode array 146 (which are part of the stimulation assembly 118 and which are configured to be used as stimulators), and one or more microphones which are not part of the stimulation assembly 118 (and which are configured to be used as sensors). For still another example, to provide electrocochleography calibration or quality assurance data, the plurality of transducers can comprise one or more actuators which are not part of the stimulation assembly 118 (and which are configured to be used as stimulators) and one or more microphones which are not part of the stimulation assembly 118 (and which are configured to be used as sensors).

Figure 4:
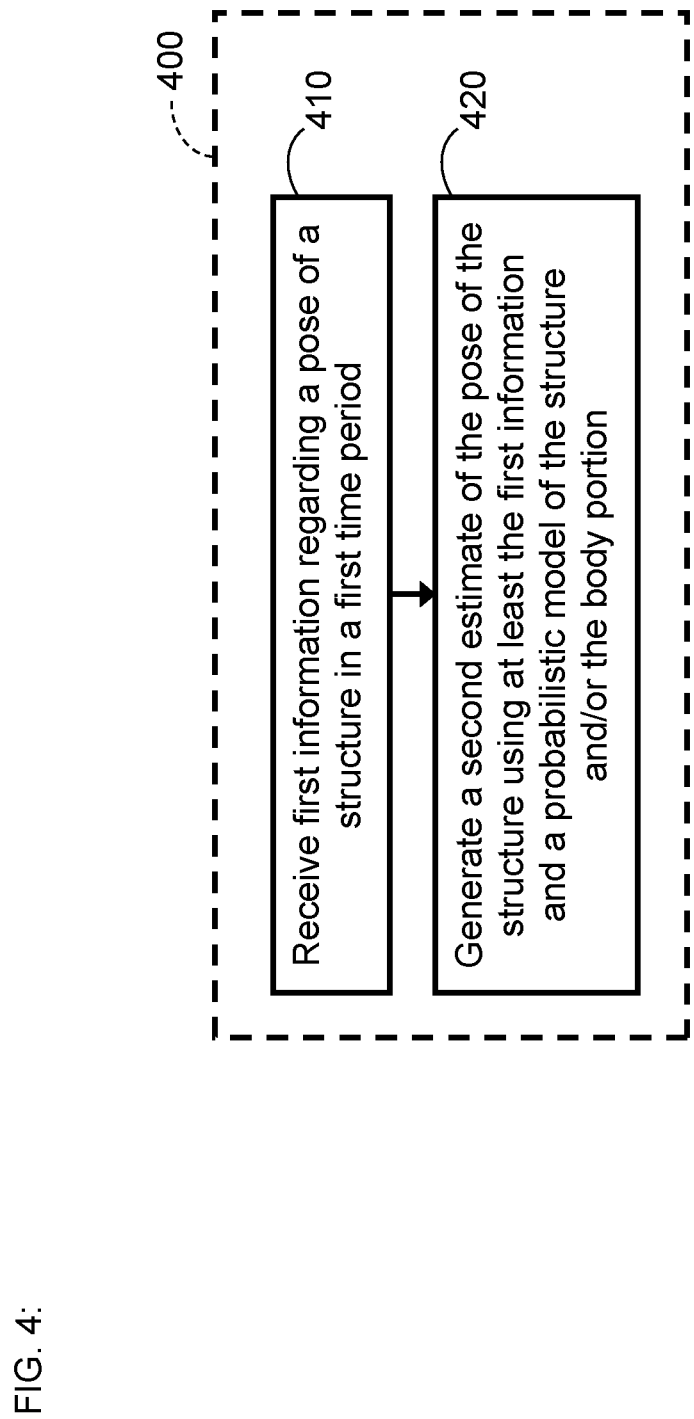
FIG. 4 is a flow diagram of an example method in accordance with certain embodiments described herein.

FIG. 4 is a flow diagram of an example method 400 in accordance with certain embodiments described herein. In an operational block 410, the method 400 comprises receiving first information regarding a pose of a structure in a first time period. The structure is configured to be inserted into a body portion of the recipient. The first information comprises at least one of a first estimate of the pose of the structure in the first time period and a first measurement set comprising one or more first measurement values. At least some of the one or more first measurement values are generated using a plurality of sensors distributed along the structure. The one or more first measurement values are indicative of the pose of the structure in the first time period. In an operational block 420, the method 400 further comprises generating a second estimate of the pose of the structure using at least the first information and a probabilistic model of the structure and/or the body portion.

In certain embodiments, the second estimate corresponds to the pose of the structure in a second time period. For example, the second time period can be same as the first time period, such that the second estimate comprises a refinement (e.g., a closer approximation of the pose of the structure in the first time period) as compared to the first estimate of the pose of the structure in the first time period. For another example, the second time period can be subsequent to the first time period, such that the second estimate comprises a new estimate of the pose of the structure in the second time period.

In certain embodiments, the structure comprises at least a portion of a medical device configured to be implanted on or within the body of the recipient. For example, the structure can comprise an array 146 (e.g., an electrode array) of a stimulation assembly 118 of the cochlear implant system 100 and the body portion into which the structure is configured to be inserted comprises a cochlea 140 of the recipient. In certain such embodiments, the pose of the structure comprises the location and/or orientation of the array 146 of the stimulation assembly 118 relative to the cochlea 140 (e.g., relative to the modiolus 240; relative to the canals 236; relative to the tonotopic regions of the cochlea 140).

In certain embodiments, the plurality of sensors comprises components of the medical device that are used during operation of the medical device after implantation is completed. For example, the plurality of sensors can comprise the stimulation elements 148 (e.g., electrodes) of the array 146 of the stimulation assembly 118. In certain other embodiments, the plurality of sensors comprises one or more sensors (e.g., electrical voltage and/or current sensors; optical sensors; vibrational sensors) that are dedicated for use during the implantation process, and that are not used during operation of the medical device after implantation is completed.

Figure 5A:
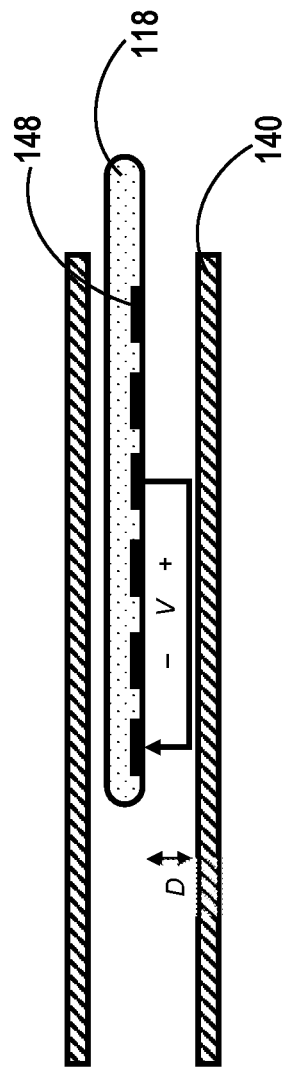
FIGS. 5A-5C schematically illustrate example voltage measurements that can be made using an electrode array of a stimulation assembly in accordance with certain embodiments described herein.
Figure 5B:
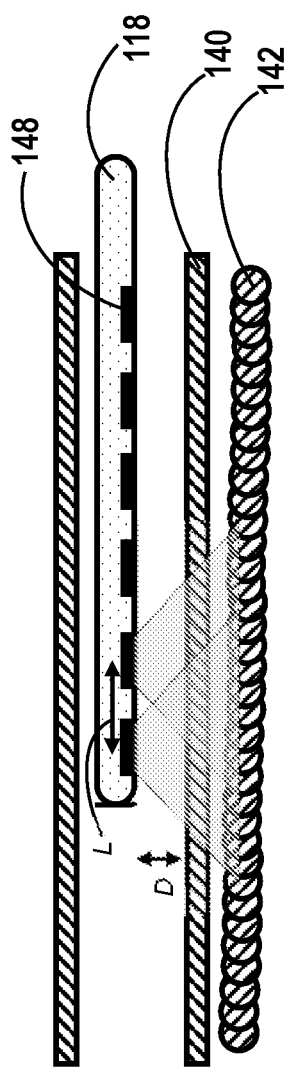
Figure 5C:
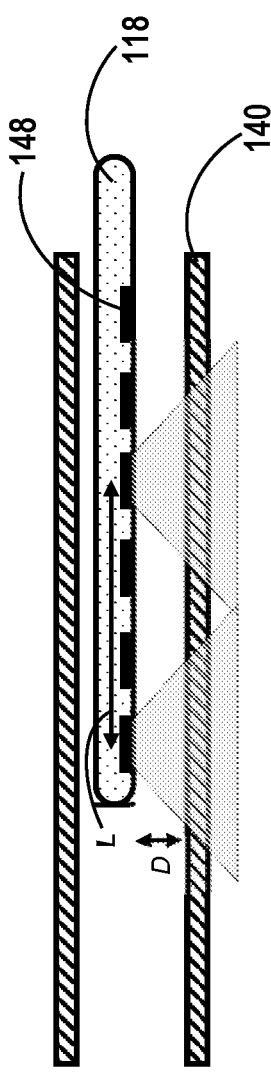

FIGS. 5A-5C schematically illustrate example voltage measurements that can be made using an array 146 of electrodes 148 of a stimulation assembly 118 to generate a measurement set comprising one or more measurement values in accordance with certain embodiments described herein. The voltage (e.g., potential difference) measurements can be taken between electrodes 148 inside and/or outside the cochlea 140 before, during, and/or after electrical stimulation (e.g., production of electrical current between electrodes 148) of the cochlea 140 by the electrodes 148. In certain embodiments, the voltage measurements are sensitive to the modiolar proximity of the electrodes 148 and/or to the linear distance between the electrodes 148 in the cochlea 140.

As schematically illustrated in FIG. 5A, four point impedance measurements can be taken by using a first pair of stimulation electrodes to stimulate the cochlear tissue and measuring the voltage between a second pair of measurement electrodes. Such measurements are sensitive to the modiolar proximity of the electrodes 148 (e.g., distance D between the electrode 148 and the modiolus 240). As the distance D decreases, the voltage V increases (see, e.g., U.S. Pat. No. 9,173,585; C.T. Tan et al., "Real-time measurement of electrode impedance during intracochlear electrode insertion," Laryngoscope, vol. 123(4), pp. 1028-1032 (2013)).

As schematically illustrated in FIG. 5B, excitation spread measurements can be taken by using a stimulation electrode to stimulate the cochlear tissue and measuring the evoked compound action potential (ECAP) response using a measurement electrode spaced from the stimulation electrode by a distance L. Larger values of L result in a decrease in the number of stimulated neurons 142 that contribute to the ECAP response detected by the measurement electrode (shown in FIG. 5B by the overlapping shaded regions), hence a decay in the signal amplitude. Such measurements are sensitive to the modiolar proximity of the electrodes 148 (e.g., distance D between the electrode 148 and the modiolus 240). When the electrodes 148 are closer to the modiolus 240 (e.g., D is smaller), the signal amplitude decay occurs more quickly and the full-width-at-half maximum (FWHM) of the ECAP response is smaller, and when the electrodes 148 are farther from the modiolus 240 (e.g., D is larger), the signal amplitude decay occurs more slowly and the FWHM of the ECAP response is larger. See, e.g., D. Degen, "*Effect of electrode position on electrophysiological and psychophysical parameters in CI patients with lateral and perimodiolar electrode arrays*," presentation at CI 2017 Pediatric 15th Symposium on Cochlear Implants in Children (Jul. 26-29, 2017).

As schematically illustrated in FIG. 5C, voltage measurements vary with the proximity of the measurement electrode to the stimulation electrode, and such voltage measurements can be used to produce a transimpedance matrix (TIM). As the distance L increases, the voltage V detected by the measurement electrode decreases, hence the corresponding values of the TIM decrease. For example, TIM measurements can be used for classifying electrode pose (e.g., whether the electrode is folded over or not; the location of the folded over electrode portion) (see, e.g., U.S. Pat. Appl. Publ. No. 2018/0140829). In addition, voltage recordings taken using one or more electrodes 148 in the cochlea 140 during electrical stimulation vary with the extent of immersion of the electrode 148 in the cochlear duct 239, due to the ability for electrical current to flow from the electrode 148 (see, e.g., U.S. Pat. No. 9,987,490).

In the example measurements of FIGS. 5A-5C, the electrodes 148 of the stimulation assembly 118 are used as transducers to both generate stimulations and to measure responses (e.g., voltages; potential differences). In certain other embodiments, one or more measurement values of a measurement set can be taken using other types of measurements which utilize other types of transducers (e.g., at least one actuator configured to generate stimulations) that are separate from the stimulation assembly 118 of the cochlear implant system 100. The measurement set of certain embodiments includes measurement values taken using a combination of the stimulation and/or measurement transducers disclosed herein.

In certain embodiments, at least one acoustic actuator can be configured to generate acoustic stimuli, and voltage measurements can be taken (e.g., using the electrodes 148 of the stimulation assembly 118) before, during, and/or after acoustic stimulation by the at least one acoustic actuator (e.g., an electrocochleography measurement). The at least one acoustic actuator can be implanted or external (e.g., in the ear canal 102), and examples of such acoustic actuators include but are not limited to: acoustic receiver; bone conduction device; middle-ear (e.g., stapes or round window) oscillator. For example, voltage measurements taken using at least one electrode 148 in the cochlea 140 before, during, and/or after acoustic stimulation vary with the mechanical freedom of the basilar membrane 244, due to the evoked hair cell response to mechanical stimulus, so such measurements can be indicative of impingement of the basilar membrane 244 by the stimulation assembly 118. See, e.g., L. Campbell et al., "*Cochlear response telemetry: intracochlear electrocochleography via cochlear implant neural response telemetry pilot study results*," Otol. Neurotol. Vol. 36(3), pp. 399-405 (2015).

In certain embodiments, acoustic or vibrational measurements can be taken, using a microphone that is implanted or external (e.g., in the ear canal 102), before, during, and/or after the production of electrical stimuli (e.g., electrical current between electrodes 148 inside and/or outside the cochlea 140) (e.g., a stapedius reflex measurement). In certain embodiments, acoustic or vibrational measurements can be taken, using a microphone that is implanted or external (e.g., in the ear canal 102), before, during, and/or after the production of acoustic stimuli (e.g., a calibration/quality assurance measurement for an electrocochleography measurement). The acoustic actuator can be implanted or external (e.g., in the ear canal 102), examples of which include but are not limited to: acoustic receiver; bone conduction device; middle-ear (e.g., stapes or round window) oscillator.

In certain embodiments, the measurement set is indicative of symmetric changes in the pose of the structure (e.g., the changes at each point of the structure are the same as one another) during insertion and/or retraction of the structure relative to the body portion. In certain other embodiments, the measurement set is indicative of asymmetric changes in the pose of the structure (e.g., the changes at two or more points of the structure are different from one another) during insertion and/or retraction of the structure relative to the body portion. For example, asymmetric changes can occur during insertion and/or retraction when the base of the electrode array moves while the apex of the electrode array does not move.

Example Uses of a Probabilistic Model

In certain embodiments, the method 400 provides a maximum likelihood estimation of the pose of the structure. The first information received in the operational block 410 can comprise a first measurement set without a prior first estimate of the pose of the structure and generating the second estimate of the pose in the operational block 420 can comprise determining an estimated pose (e.g., a most likely pose) of the structure without prior knowledge of a previous estimate of the pose of the structure. For example, an estimated pose of an electrode array 146 can be determined using a probabilistic model (e.g., a canonical model) without prior knowledge based on a measurement set of collected measurement values of the electrode impedances to ground for a plurality of electrodes 148 of the electrode array. In certain embodiments, the maximum likelihood estimation can use various mathematical techniques (e.g., Monte Carlo; particle filters; Kalman filters; recursive Bayesian estimation) to produce the estimated pose of the structure. An estimate of the pose can be generated based on the probabilistic model. For example, the probability distribution for the various possible poses can be analyzed to derive an estimate of the pose corresponding to the mean, median, mode, and/or center-of-mass of the probability distribution and/or the uncertainty (e.g., standard deviation; interquartile range) of the probability distribution.

Figure 6A:
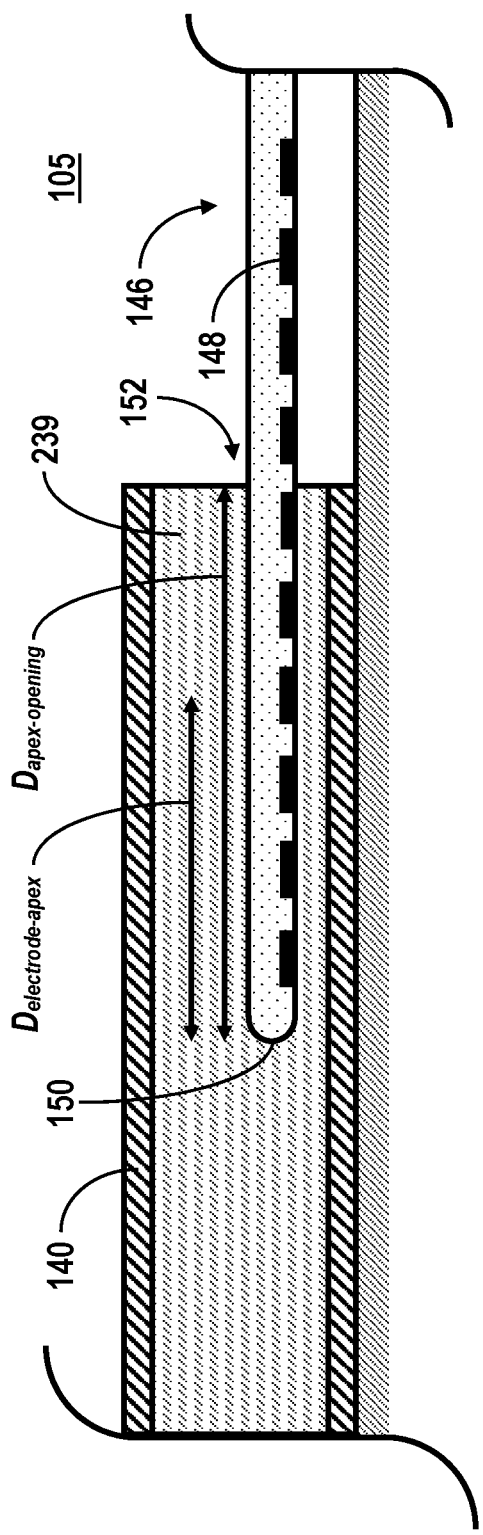
FIG. 6A schematically illustrates an example canonical model of the structure and/or the body portion in accordance with certain embodiments described herein.

FIGS. 6A-6J schematically illustrate an example use of a canonical model of the structure and/or the body portion in accordance with certain embodiments described herein. FIG. 6A schematically illustrates a canonical model (e.g., probabilistic model) in which an elongate array 146 of stimulation elements 148 (e.g., an electrode array of electrodes) is inserted into a cochlea 140 through the middle ear 105 in accordance with certain embodiments described herein. In certain embodiments, the cochlea 140 is modelled as a tube containing a conductive liquid, and the middle ear 105 is modelled as a cavity containing an insulating gas. The electrodes 148 are distributed along the length of the array 146, and can be characterized by their distance $D_{electrode-apex}$ from an apex 150 of the array 146. The pose of the array 146 can be described by the distance $D_{apex\text{-}opening}$ between an apex 150 of the array 146 and an opening 152 (e.g., a cochleostomy 122 formed through the round window 121, the oval window 112, the promontory 123, or through an apical turn 147 of the cochlea 140) through which the array 146 enters the cochlea 140. The impedance between each electrode 148 and a remote ground potential can be predicted based on the pose of the array 146. Electrodes 148 inside the cochlea 140 can be predicted to be connected to the remote ground potential by a conductive path, corresponding to a predicted low impedance, and electrodes 148 outside of the cochlea 140 correspond to a predicted high impedance.

In certain embodiments, the predicted measurement value of the impedance is derived from a map of the anatomy of the body portion (e.g., the cochlear duct 239). For example, the pose of the array 146 in the cochlear duct 239 can be described by the distance $D_{apex\text{-}opening}$ between the apex 150 of the array 146 and the opening 152 to the cochlea 140. The location of each electrode 148 within the cochlear duct 239 can be computed based on the distance $D_{electrode\text{-}apex}$ between the electrode 148 and the apex 150 of the array 146. The impedance between the electrode 148 and a remote ground potential can be predicted (e.g., by looking up the location of the electrode 148 in a map of predicted impedances to a remote ground potential).

Figure 6B:
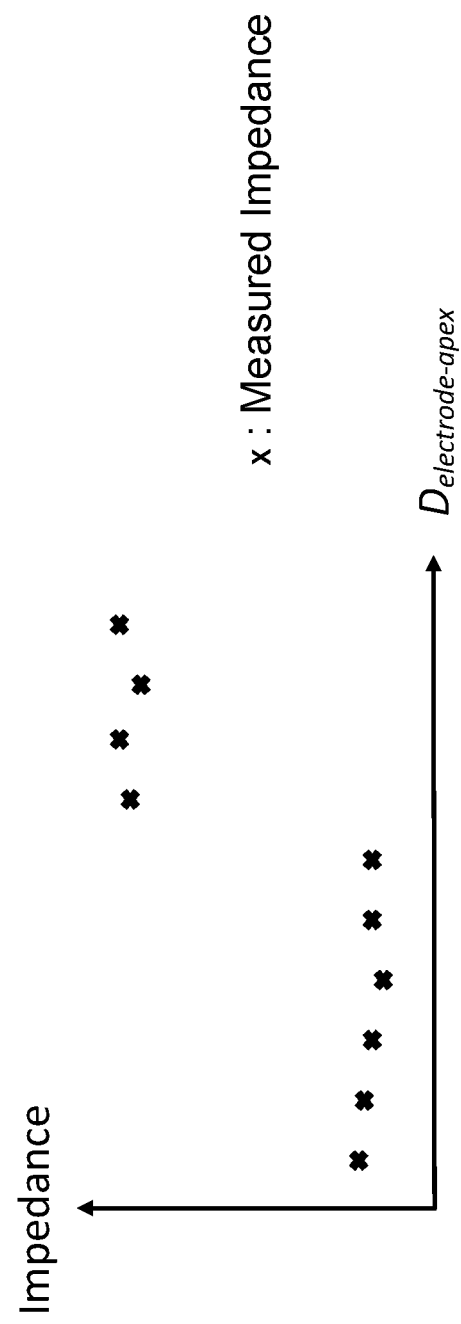
FIG. 6B schematically illustrates an example plot of observations in accordance with certain embodiments described herein.

In certain embodiments, the impedance between each electrode 148 and the remote ground potential is observed (e.g., measured). FIG. 6B schematically illustrates an example plot of such observations (e.g., measured impedances as a function of $D_{electrode\text{-}apex}$) in accordance with certain embodiments described herein. The measured impedances of FIG. 6B from the plurality of electrodes 148 appear to adhere to the expectations of the probabilistic model of FIG. 6A, in which a demarcation between the electrodes 148 outside the cochlea 140 and the electrodes 148 inside the cochlea 140 is between the sixth and seventh electrodes 148 from the apex 150 (e.g., the first through sixth electrodes 148 are within the cochlea 140 and the seventh through the "n−1"th electrodes 148 are outside the cochlea 140). These observations can be compared to predictions using a variety of metrics, including but not limited to: root mean square of the differences, arithmetic mean, and maximum absolute difference. In certain embodiments, the predicted and observed values are transformed before making such a comparison. For example, impedances can be coded as 0 if they fall beneath a predetermined threshold impedance $Z_{threshold}$, and coded as 1 otherwise.

Figure 6C:
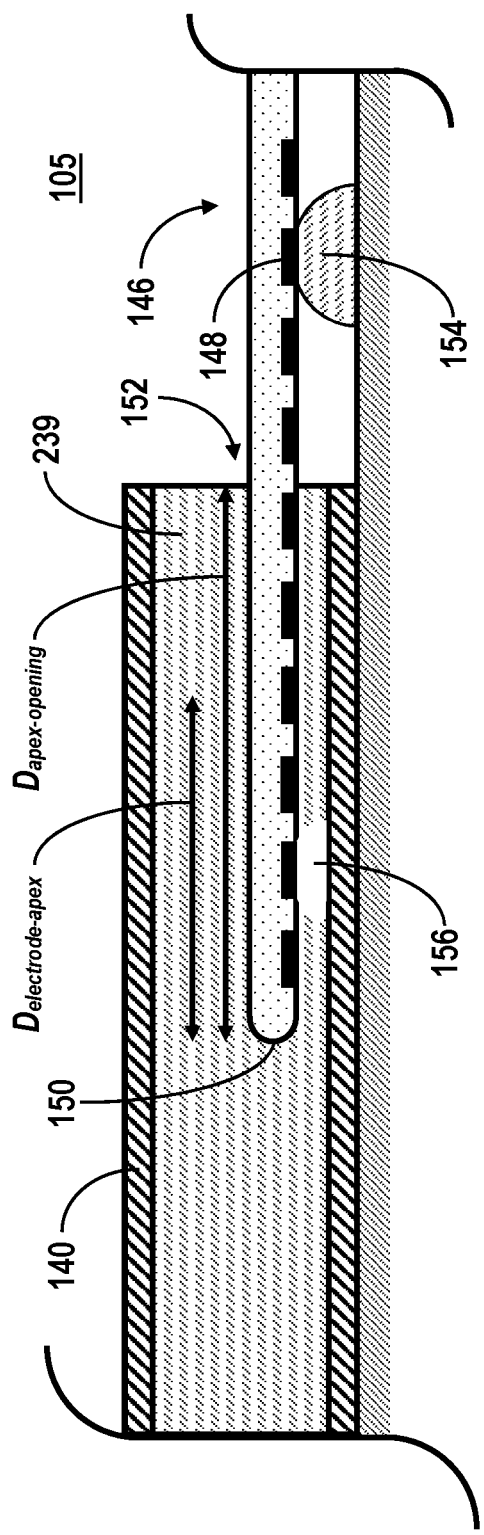
FIG. 6C schematically illustrates the example canonical model of the structure and/or body portion of FIG. 6A with examples of other physical factors in accordance with certain embodiments described herein.

However, other physical factors can potentially affect the ground impedance measurement values from the electrodes 148 and the estimated pose of the array 146. FIG. 6C schematically illustrates the canonical model (e.g., probabilistic model) structure of FIG. 6A with examples of such physical factors in accordance with certain embodiments described herein. For example, as shown in FIG. 6C, an electrode 148 outside the cochlea 140 can be shorted to the ground potential (e.g., via a bead of fluid 154 or via a surgical instrument, such as forceps, being used to insert the array 146 into the cochlea 140). For another example, as shown in FIG. 6C, an electrode 148 inside the cochlea 140 can be open from the ground potential (e.g., due to an air bubble 156 between the electrode 148 and the surrounding structure of the cochlear duct 239 or wire damage between the electrode 148 and the internal component 144 of the auditory prosthesis 100), thereby providing a high ground impedance measurement value. As shown in FIG. 6C, the array 146 has six electrodes 148 inside the cochlea 140, with an air bubble 156 on the second electrode 148 from the apex 150, and four electrodes 148 outside the cochlea 140, with a bead of fluid 154 on the ninth electrode 148 from the apex 150.

Figure 6D:
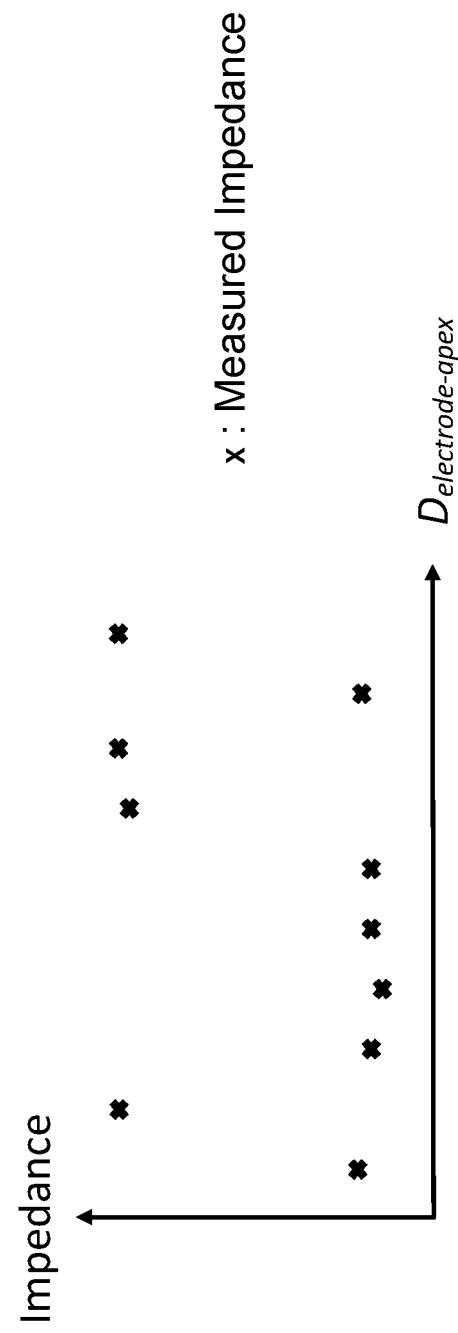
FIG. 6D schematically illustrates an example plot of the measured impedances as a function of $D_{electrode-apex}$ from the array of FIG. 6C in accordance with certain embodiments described herein.

FIG. 6D schematically illustrates an example plot of the measured impedances as a function of $D_{electrode\text{-}apex}$ from the array 146 of FIG. 6C in accordance with certain embodiments described herein. The measured impedances from at least some of the electrodes 148 do not adhere to the expectations of the probabilistic model of FIG. 6A due to aberrations (e.g., artifacts) caused by the physical factors schematically illustrated by FIG. 6C. For example, in FIG. 6D, the measured impedance from the second electrode 148 from the apex 150 is affected by the air bubble 156 and the measured impedance from the ninth electrode 148 from the apex 150 is affected by the bead of liquid 154. As a result of the potential influence of such physical factors, the pose of the array 146 (e.g., the location of the demarcation between the electrodes 148 outside and inside the cochlea 140) can be unclear from merely inspecting the measured impedances. For example, in FIG. 6D, in view of the existence of aberrations (e.g., artifacts), mere inspection of the measured impedances is unable to determine the pose (e.g., location of the demarcation) with a desired level of precision (e.g., more precisely than somewhere in a range of multiple poses, such as the demarcation being within a range of the sixth electrode 148 through the tenth electrode 148).

Figure 6E:
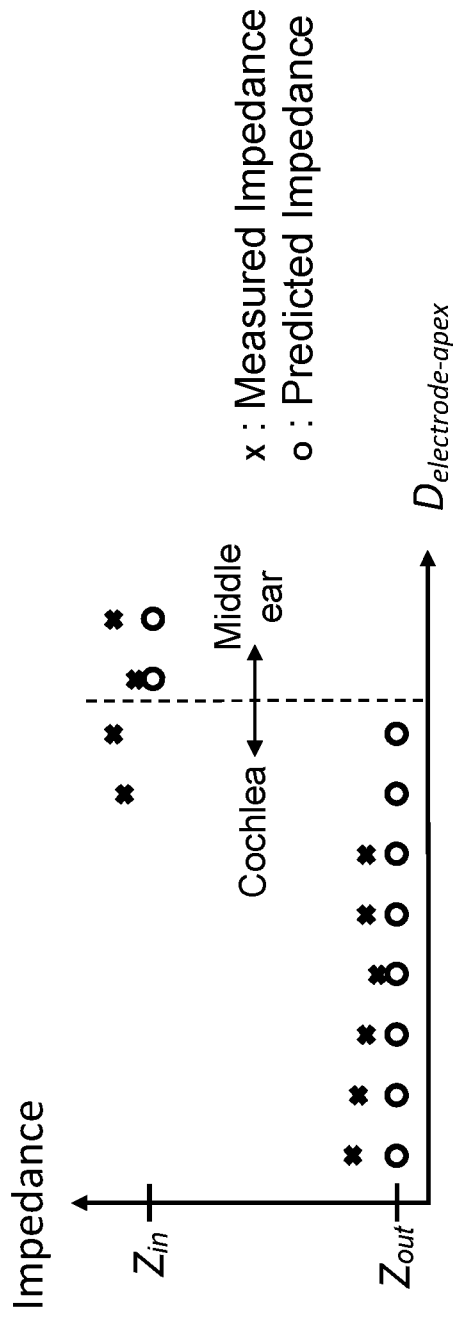
FIG. 6E schematically illustrates a plot of a first set of observed impedance values (e.g., unaffected by the physical factors shown in FIG. 6C) compared to a set of predicted impedance values for a first pose of the array in accordance with certain embodiments described herein.
Figure 6F:
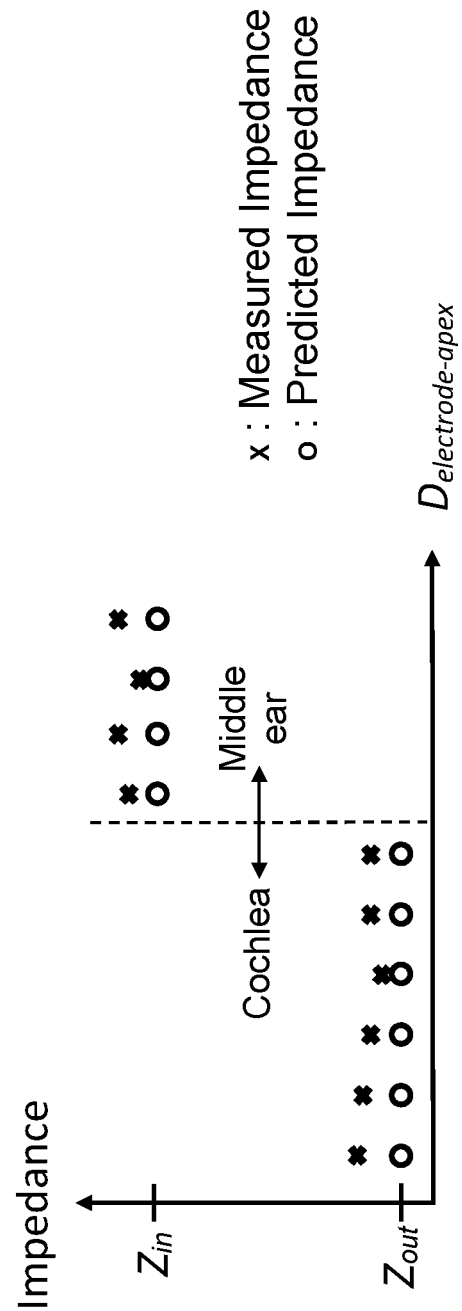
FIG. 6F schematically illustrates a plot of the first set of observed impedance values of FIG. 6E compared to a set of predicted impedance values for a second pose of the array in accordance with certain embodiments described herein.

FIG. 6E schematically illustrates a plot of a first set of observed impedance values (e.g., unaffected by the physical factors shown in FIG. 6C) compared to a set of predicted impedance values for a pose of the array 146 in which the eighth electrode 148 is inside the cochlea 140 and the ninth electrode 148 is outside the cochlea 140 (e.g., the opening 152 is between the eighth and ninth electrodes 148) in accordance with certain embodiments described herein. FIG. 6F schematically illustrates a plot of the first set of observed impedance values of FIG. 6E compared to a set of predicted impedance values for a pose of the array 146 in which the sixth electrode 148 is inside the cochlea 140 and the seventh electrode 148 is outside the cochlea 140 (e.g., the opening 152 is between the sixth and seventh electrodes 148) in accordance with certain embodiments described herein.

FIGS. 6E and 6F are two examples of the predicted impedance values for different poses of the array 146 during an insertion into the cochlea 140 under the canonical model in which the array 146 is considered to be in one of n states depending on how many of the n−1 electrodes 148 of the array 146 are within the cochlea 140. For example, a first state corresponds to none of the electrodes 148 within the cochlea 140, a second state corresponds to only the electrode 148 closest to the apex 150 within the cochlea 140, a third state corresponds to the two electrodes 148 closest to the apex 150 within the cochlea 140, . . . , and a $n^{th}$ state corresponds to all n−1 electrodes 148 within the cochlea 140. Each state corresponds to a set of ground impedance measurement values $Z_1 \ldots Z_{n-1}$ expected to be obtained from the plurality of electrodes 148. For example, for each state, electrodes 148 that are inside the cochlea 140 are expected to provide ground impedance measurement values equal to a common value $Z_{in}$ (e.g., less than a first predetermined ground impedance threshold $Z_{threshold\text{-}1}$) and electrodes 148 that are outside the cochlea 140 are expected to provide ground impedance measurement values equal to a common value $Z_{out}$ (e.g., greater than a second predetermined ground impedance threshold $Z_{threshold\text{-}2}$). In certain embodiments, the first predetermined ground impedance threshold $Z_{threshold-1}$ and the second predetermined ground impedance threshold are equal to one another, while in certain other embodiments, the first and second predetermined ground impedance thresholds are different from one another.

Figure 6G:
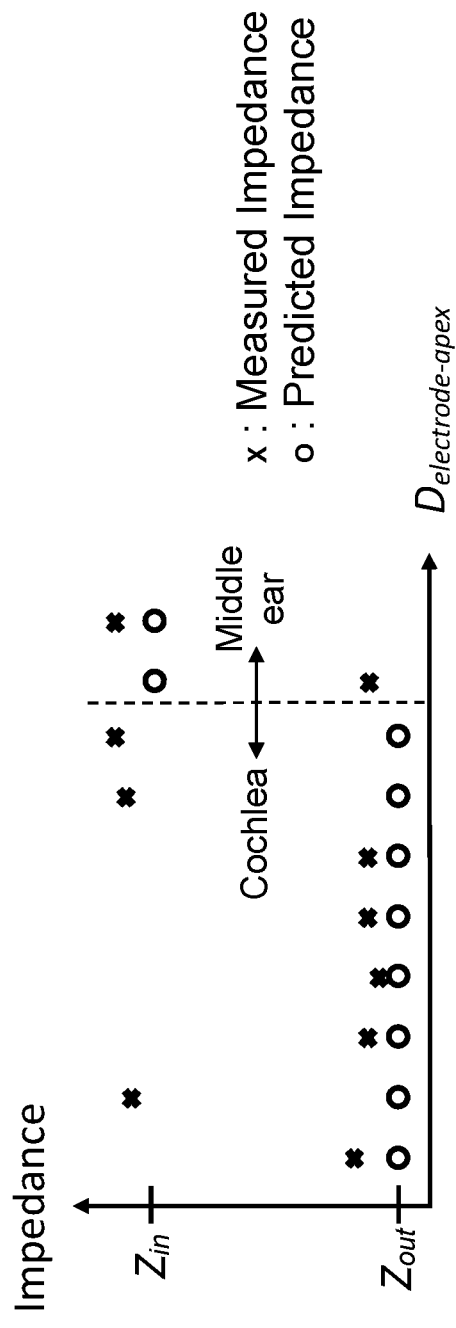
FIG. 6G schematically illustrates a plot of a second set of observed impedance values (e.g., affected by the physical factors shown in FIG. 6C) compared to the same set of predicted impedance values of FIG. 6E in accordance with certain embodiments described herein.
Figure 6H:
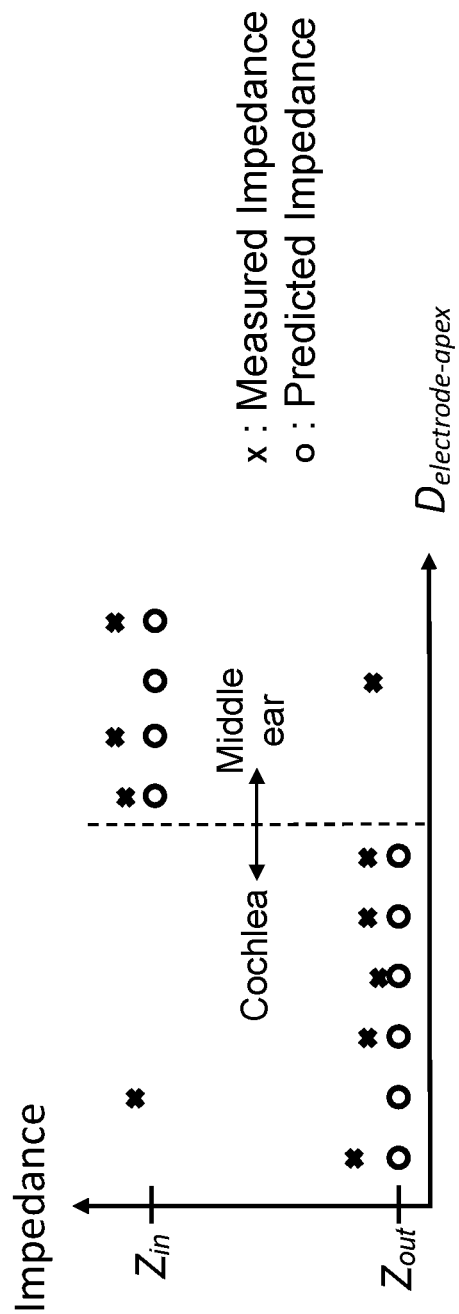
FIG. 6H schematically illustrates a plot of the second set of observed impedance values of FIG. 6G compared to the same set of predicted impedance values of FIG. 6F in accordance with certain embodiments described herein.

FIG. 6G schematically illustrates a plot of a second set of observed impedance values (e.g., affected by the physical factors shown in FIG. 6C) compared to the same set of predicted impedance values of FIG. 6E. FIG. 6H schematically illustrates a plot of the second set of observed impedance values of FIG. 6G compared to the same set of predicted impedance values of FIG. 6F.

In certain embodiments, a collection of possible poses is used to generate predictions of possible measurements, and each set of predictions is compared to a set of possible measurement values. For example, error metrics resulting from each comparison can be used to estimate a likelihood of a pose (e.g., by direct computation). In certain embodiments, the likelihood has an inverse relationship with the error metric (e.g., the likelihood is estimated as $$\frac{1}{\text{error} + 1}$$

or $e^{-error}$).

Figure 6I:
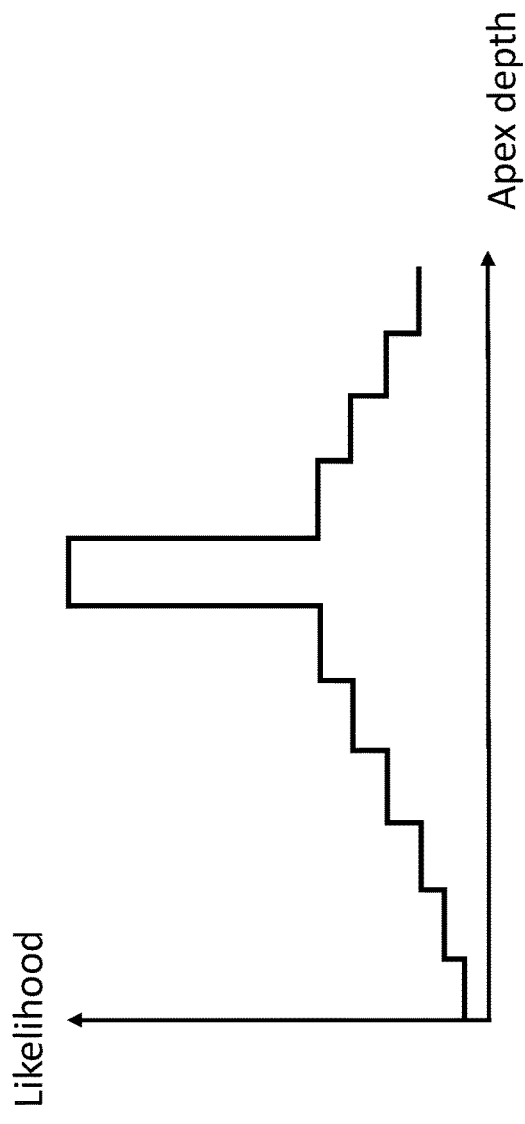
FIGS. 6I and 6J schematically illustrate two examples of the calculated likelihoods for a range of possible poses in accordance with certain embodiments described herein.
Figure 6J:
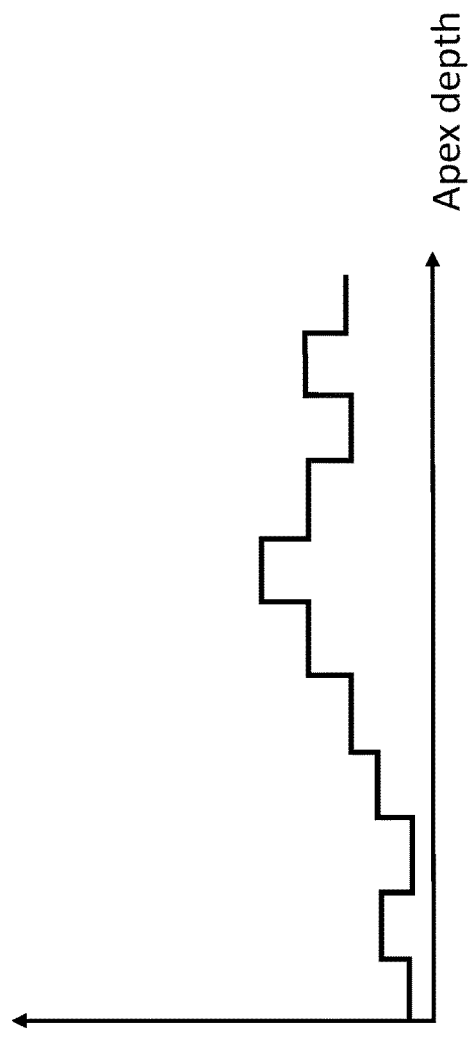

FIGS. 6I and 6J schematically illustrate two examples of the calculated likelihoods for a range of possible poses in accordance with certain embodiments described herein. FIG. 6I corresponds to comparisons of the first set of observed impedance values of FIGS. 6E and 6F (e.g., unaffected by the physical factors shown in FIG. 6C) with various sets of predicted impedance values for various poses of the array 146 (e.g., as shown in FIGS. 6E and 6F). FIG. 6I shows a clear peak of likelihood for poses which place the sixth electrode 148 inside the cochlea 140 and the seventh electrode 148 outside the cochlea 140 (e.g., the opening 152 between the sixth and seventh electrodes 148), with a monotonic decrease of the likelihood as the depth moves away from this range.

FIG. 6J corresponds to comparisons of the second set of observed impedance values of FIGS. 6G and 6H (e.g., affected by the physical factors shown in FIG. 6C) with various sets of predicted impedance values for various poses of the array 146 (e.g., as shown in FIGS. 6G and 6H). FIG. 6J shows that the peak still exists for poses which place the sixth electrode 148 inside the cochlea 140 and the seventh electrode 148 outside the cochlea 140, but the peak is less pronounced and there are minor likelihood peaks near the second electrode 148 and the ninth electrode 148, both of which are affected by artifacts of FIG. 6C. The peak near the second electrode 148 is significantly lower than the peak near the ninth electrode 148, due to the four low-impedance electrodes 148 that are necessarily outside the cochlea 140 if the second electrode 148 is outside the cochlea 140.

In certain embodiments, an estimated pose of the array 146 can be computed based on the calculated likelihoods. For example, the pose with the highest likelihood can be selected (e.g., a maximum likelihood estimation can be used), or poses with a numerical metric (e.g., depth in millimeters) can be combined to produce an estimate (e.g., computing a mean or median pose).

In certain embodiments, the calculated likelihood for a pose of the array 146 is combined with a prior calculated probability for the pose of the array 146 to compute a posterior probability for a pose of the array 146. For example, at initialization, all poses or a subset of all poses of the array 146 can be considered to be equally probable. Based on the calculated posterior probabilities, an estimated pose of the array 146 can be computed. For example, the pose with the highest likelihood can be selected (e.g., a maximum a posteriori estimation), or poses with a numerical metric (e.g., depth in millimeters) can be combined to produce an estimate (for example, computing a mean or median pose).

In certain embodiments, the method 400 provides a maximum a posteriori estimation of the pose of the structure. The first information received in the operational block 410 can comprise a first estimate of the pose of the structure in the first time period and a first measurement set, and generating a second estimate of the pose of the structure in the operational block 420 can comprise updating the first estimate in response to the first measurement set. For example, an estimated pose (e.g., a most likely pose) of the electrode array 146 can be determined using a probabilistic model (e.g., a canonical model) and at least one previous estimated pose of the electrode array 146 based on the measurement set of collected measurement values of the electrode impedances to ground for a plurality of electrodes 148 of the electrode array. A probability of each possible state can be scaled by the distance D of its demarcation location from that of a prior estimated pose (e.g., the probability can be multiplied by a factor 1/(1+D), where D is the distance in millimeters from the demarcation location of the immediately-preceding estimated pose). In certain such embodiments, the maximum a posteriori estimation can use various mathematical techniques (e.g., Monte Carlo; particle filters; Kalman filters; recursive Bayesian estimation) to generate the second estimate of the pose of the structure.

In certain embodiments, the probabilistic model can be adjusted (e.g., different states weighted differently relative to one another) based on other information generated during the implantation process. For example, the probabilistic model can be adjusted based at least in part on measurement values generated by at least one other sensor that is responsive to the pose of the structure. An example of such a sensor includes but is not limited to an accelerometer mechanically coupled to the structure, to a sheath or stylet mechanically coupled to the structure, to a tool (e.g., tweezers) being used to manipulate the structure, and/or to a virtual reality system being used by the medical professional.

For another example, the probabilistic model can be adjusted based at least in part on manipulation control signals that are known to have been sent to an implantation actuator (e.g., a surgical robot) which is directly or indirectly manipulating the electrode array 146. For example, for manipulation control signals corresponding to forward advancement of the electrode array 146 into the cochlea 140, the probability for a state in which forward advancement had occurred would be considered to be more probable than the probability for a state in which the electrode array 146 had moved backward. In certain embodiments, the probabilistic model can include consideration of the likelihood of device faults (e.g., open or short-circuited electrodes 148).

In certain embodiments, the cumulative estimates of the pose and/or the collected measurements can be used to map the anatomy of the body portion (e.g., the cochlear duct) and/or to refine (e.g., update) an existing map. The map can be initialized based on pre-operative images (e.g., from magnetic resonance imaging). For example, the measurement values (e.g., observed impedances to a remote ground) can be combined with (e.g., added to) a map of the anatomy based on the estimated pose. In certain embodiments, the cumulative estimates of the pose and/or the collected measurements are used to refine the logic applied during the calculation of pose likelihood. For example, the threshold $Z_{threshold-1}$ can be increased by a fixed step dZ if all electrodes 148 estimated to be inside the cochlea 140 have an impedance above $Z_{threshold-1}$+dZ.

Figure 7A:
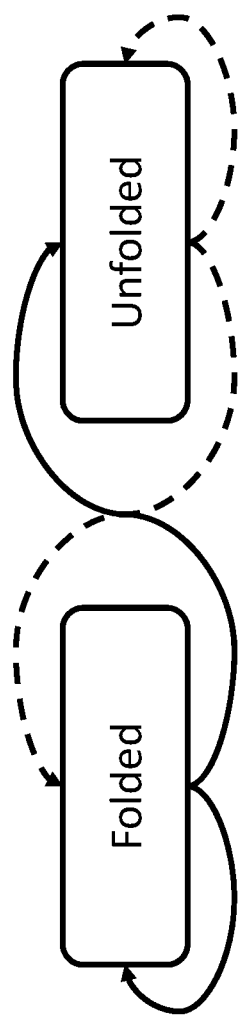
FIGS. 7A-7C schematically illustrate another example use of a canonical model of the structure and/or the body portion in accordance with certain embodiments described herein.
Figure 7B:
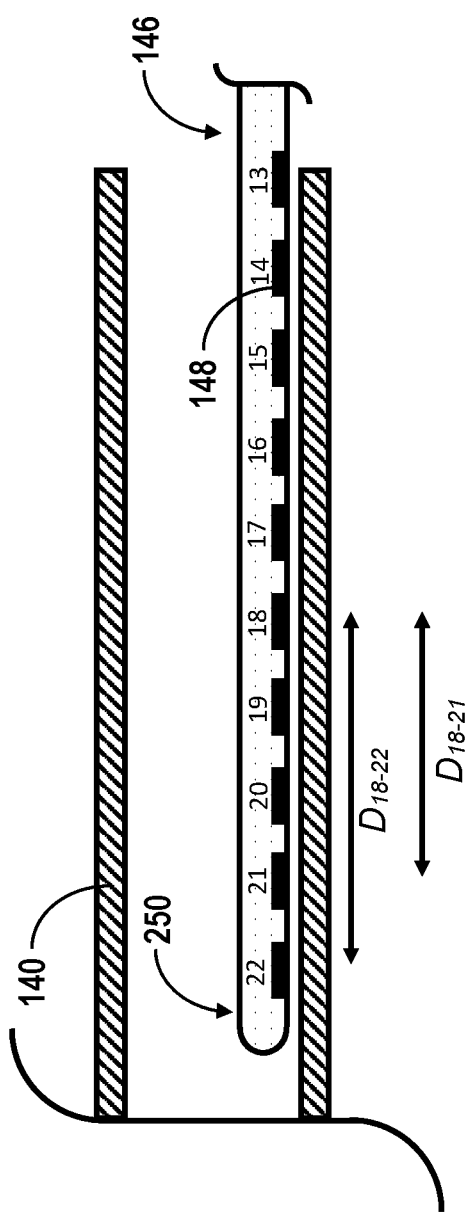
Figure 7C:
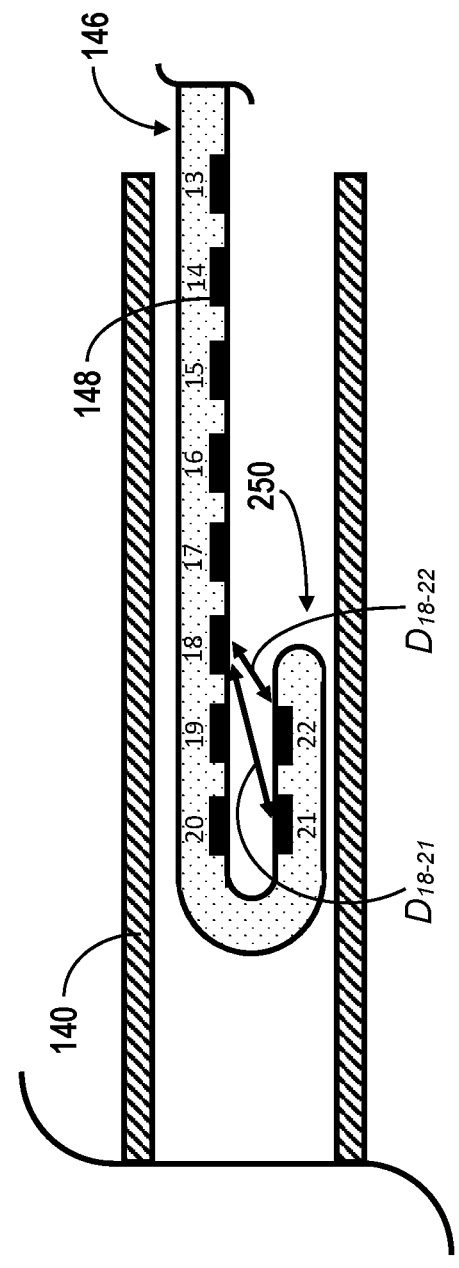

FIGS. 7A-7C schematically illustrate another example use of a canonical model of the structure and/or the body portion in accordance with certain embodiments described herein. The example of FIGS. 7A-7C is applicable to detection of a folded-over state of an apical portion 250 of an electrode array 146. FIG. 7A illustrates an example state diagram with two states for an electrode array 146 (e.g., a pre-curved electrode array 146) being inserted into a cochlea 140. In an "unfolded" state (e.g., alternatively referred to as a "modiolar-proximal" or "modiolar-hugging" state), as schematically illustrated by FIG. 7B), the electrode array 146 extends in a single direction along the canals 236 (e.g., is optimally positioned relative to the electrode base or modiolus 240). In a "folded" state, schematically illustrated by FIG. 7C, at least a portion of the electrode array 146 extends away from the electrode base and the apical portion 250 extends towards the modiolus 240, with an acute angle (e.g., bend; kink) between the two portions. In certain other embodiments, the canonical model can include a third state for the electrode array 146, between the "unfolded" state and the "folded" state, in which a portion of the electrode array 146 extends away from the electrode base and the apical portion 250 extends towards the modiolus 240, with an obtuse angle (e.g., bend; kink) between the two portions (e.g., referred to as a "snagged" state).

As shown in FIG. 7A, the pose of the electrode array 146 can transition (e.g., from a time $t_1$ to a time $t_2>t_1$) among the states of the canonical model during insertion into the cochlea 140 (e.g., while advancing the electrode array 146 apically into the cochlea 140 and/or withdrawing the electrode array 146 basally from the cochlea 140). For example, for the two-state canonical model of FIG. 7A, from the "unfolded" state, the electrode array 146 can either remain in the "unfolded" state (e.g., inserted deeper into the cochlea 140) or can transition to the "folded" state. From the "folded" state, the electrode array 146 can either remain in the "folded" state or can transition to the "unfolded" state. For a canonical model further comprising the "snagged" state between the "unfolded" state and the "folded" state, the electrode array 146 in the "unfolded" state can either remain in the "unfolded" state or can transition to the "snagged" state, the electrode array 146 in the "snagged" state can remain in the "snagged" state, transition to the "folded" state, or transition to the "unfolded" state, and the electrode array 146 in the "folded" state can remain in the "folded" state or can transition to the "snagged" state.

In certain embodiments, each of the states of the canonical model describes a collection of poses of the electrode array 146 that affect the measurement values (e.g., from the electrodes 148). Measurement values that are indicative of the distances between electrodes include, but are not limited to, transimpedance measurement values. For example, referring to FIG. 7B, the "unfolded" state can describe a collection of poses in which the distance $D_{18-22}$ between electrode 18 and electrode 22 is greater than the distance $D_{18-21}$ between electrode 18 and electrode 21 and the transimpedance $Z_{18-22}$ between electrode 18 and electrode 22 is expected to be less than the transimpedance $Z_{18-21}$ between electrode 18 and electrode 21. Conversely, referring to FIG. 7C, the "folded" state can describe a collection of poses in which the distance $D_{18-21}$ between electrode 18 and electrode 21 is greater than the distance $D_{18-22}$ between electrode 18 and electrode 22 and the transimpedance $Z_{18-22}$ between electrode 18 and electrode 22 is expected to be greater than the transimpedance $Z_{18-21}$ between electrode 18 and electrode 21.

The probabilities for each of these states can be estimated by comparing the expectations of the canonical model against the measurement values generated by the electrodes 148. By comparing the probabilities of a pose to other possible poses, which each have their own expected measurement values, the pose of the electrode array 146 can be estimated, or partially estimated, based on the most likely pose.

Figure 8:
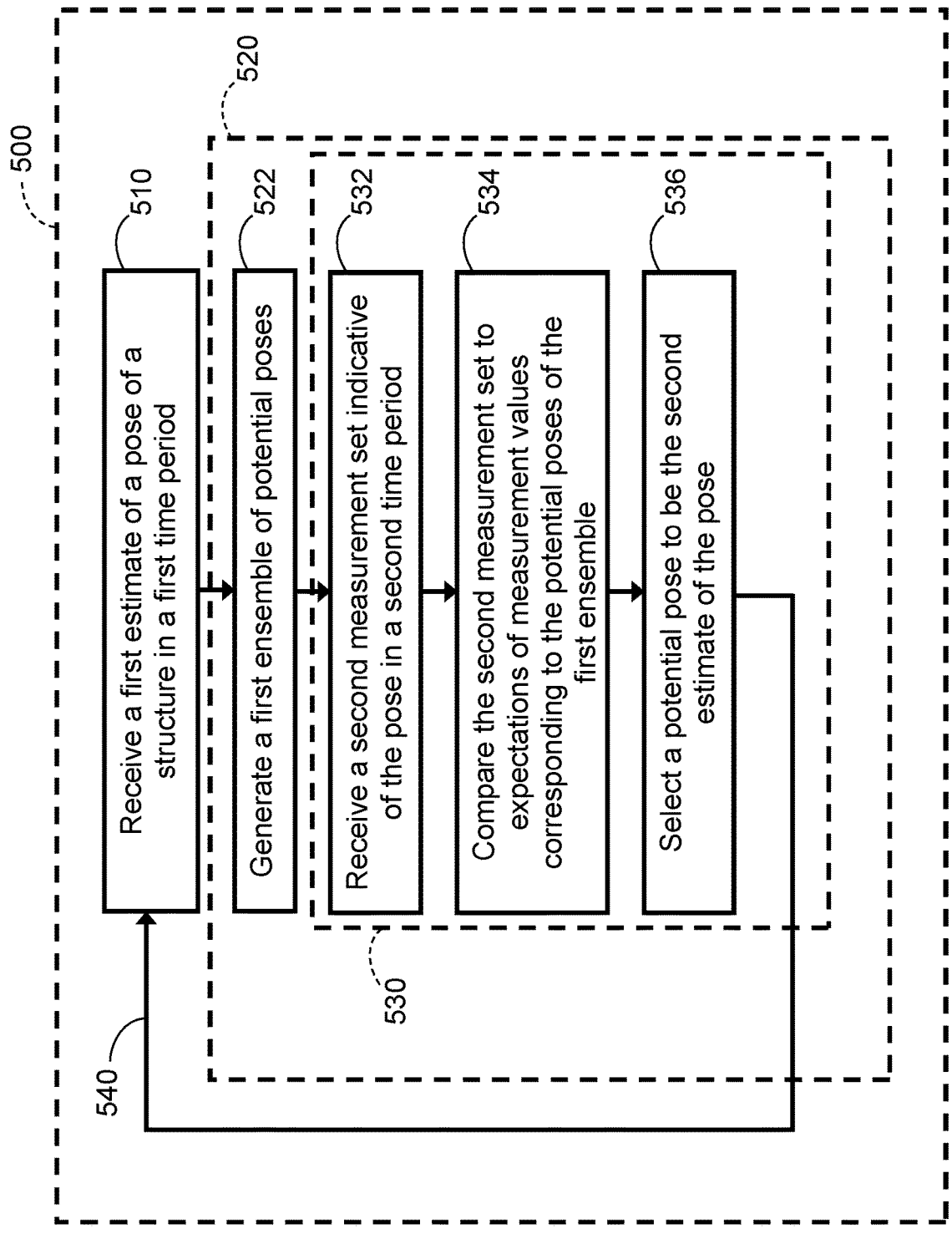
FIG. 8 is a flow diagram of an example method that compares measurement values to an ensemble of potential poses generated using the probabilistic model of the structure in accordance with certain embodiments described herein.
Figure 9:
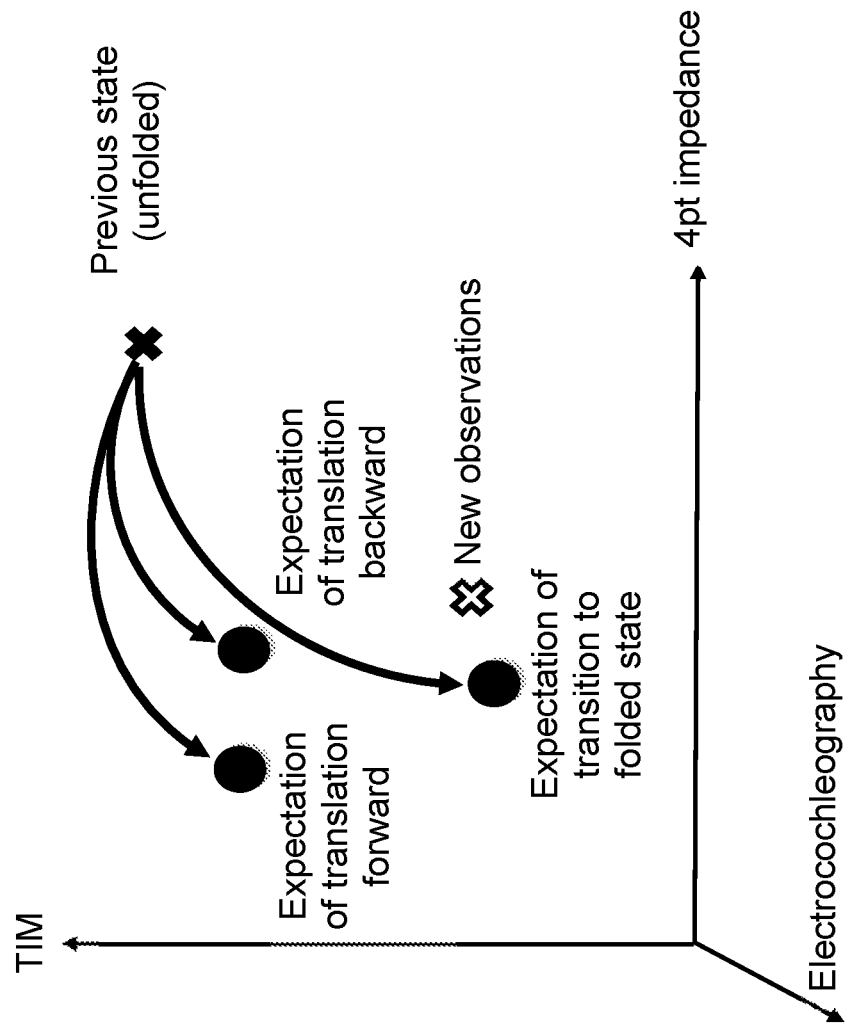
FIG. 9 schematically illustrates an example evaluation of pose evolution of an array being inserted into a cochlea in accordance with certain embodiments described herein.

FIG. 8 is a flow diagram of an example method 500 that compares measurement values to an ensemble of potential poses generated using the probabilistic model of the structure in accordance with certain embodiments described herein. FIG. 9 schematically illustrates an example evaluation of pose evolution of an array 146 being inserted into a cochlea 140 in accordance with certain embodiments described herein. The pose evolution of FIG. 9 corresponds to an evolution from a first state (e.g., previous state; state in a first time period $\leq t_1$) to a second state (e.g., new state; state in a second time period $>t_1$) state in accordance with certain embodiments described herein.

In an operational block 510, the method 500 comprises receiving first information regarding the pose of the structure relative to the body portion of the recipient in a first time period (e.g., the pose at a time $\leq t_1$). The first information comprises at least one of a first estimate of the pose of the structure in the first time period and a first measurement set (e.g., comprising measurement values generated in the first time period by the plurality of sensors distributed along the structure). As schematically illustrated in FIG. 9, the first state is denoted by a black cross that corresponds to metrics derived from the TIM, four-point impedance, and/or electrocochleography measurements in the first time period.

In an operational block 520, the method 500 further comprises generating a second estimate of the pose of the structure in the second time period (e.g., the pose at a time $>t_1$). For example, generating the second estimate can comprise, in an operational block 522, generating a first ensemble of potential poses of the structure in the second time period using the probabilistic (e.g., canonical) model of the structure and/or the body portion. In the example schematically illustrated in FIG. 9, the first state of the array 146 is an "unfolded" (e.g., "modiolar-proximal") state, and corresponds to particular observations (e.g., measurement values) from one or more measurements (e.g., TIM measurements, examples of which include TIM gradient measurements; voltage measurements; impedance measurements; four-point impedance measurements; electrocochleography measurements) generated in the first time period (e.g., at a time $\leq t_1$). The first ensemble of potential poses generated using the probabilistic (e.g. canonical) model of FIGS. 7A-7C can comprise: (i) a potential pose in which the array 146 remains in the "unfolded" state and is translated forward (e.g., further into) the cochlea 140, (ii) a potential pose in which the array 146 remains in the "unfolded" state and is translated backward (e.g., further out of) the cochlea 140, and (iii) a potential pose in which the array 146 transitions to a "folded" state. In certain embodiments, the first ensemble can further comprise a potential pose in which the array 146 remains unmoved (e.g., still in the first state). In certain embodiments, generating the first ensemble of potential poses further comprises generating (e.g., calculating) expectations of measurement values corresponding to the potential poses of the first ensemble (denoted by black circles in FIG. 9).

In certain embodiments, generating the second estimate in the operational block 520 can further comprise, in an operational block 530, selecting the second estimate of the pose from the first ensemble of potential poses. For example, as shown in FIG. 8, selecting the second estimate in the operational block 530 can comprise, in an operational block 532, receiving a second measurement set comprising one or more second measurement values. At least some of the one or more second measurement values are generated using the plurality of sensors and are indicative of the pose of the structure in the second time period subsequent to the first time period (e.g., time $>t_1$). Selecting the second estimate in the operational block 530 can further comprise, in an operational block 534, comparing the second measurement set to the expectations of measurement values corresponding to the potential poses of the first ensemble and, in an operational block 536, selecting, based on said comparing, a potential pose of the first ensemble to be the second estimated pose.

For example, new observations (e.g., measurement values) generated at time $t_2>t_1$, denoted in FIG. 9 by a white cross, correspond to the new state of the array 146 and can be compared to expectations of the measurement values for the various poses of the first ensemble of potential poses. Referring to FIG. 9, the new observations can be compared to: (i) the expectation of measurement values for the array 146 remaining in the "unfolded" state while having translated forward into the cochlea 140, (ii) the expectation of measurement values for the electrode array 146 remaining in the "unfolded" state while having translated backward out of the cochlea 140, and (iii) the expectation of measurement values for the electrode array 146 transitioning into the "folded" state. In certain embodiments, the new observations can also be compared to the expectation of measurement values for the array 146 remaining unmoved (e.g., still in the first state). In the example of FIG. 9, the new observations are closer to the expectation of measurement values for the array 146 transitioning into the "folded" state, so the second state can be considered to be the "folded" state.

In certain embodiments, the second estimate of the pose is subsequently used as the first estimate of the pose (e.g., as denoted by the arrow 540 in FIG. 8) for a subsequent estimation of the pose (e.g., to continually estimate the pose of the structure during the implantation process). For example, the method 500 can comprise generating a second ensemble of potential poses of the structure in a third time period after the second time period, the second ensemble generated using the probabilistic model, and selecting a third estimate of the pose from the second ensemble of potential poses (e.g., by comparing a third measurement set indicative of the pose in the third time period to expectations of measurement values corresponding to the potential poses of the second ensemble, and selecting a potential pose to be the third estimate of the pose).

In certain embodiments, the estimates of the pose generated using measurement sets generated during implantation and/or retraction of the structure into and/or from the body portion are used to facilitate implantation and/or retraction of the structure. The estimates of the pose can be used by the system 300 of FIG. 3 to generate at least one status reporting signal (e.g., information 342 regarding the estimated pose, symmetric changes of the pose, and/or asymmetric changes of the pose). In certain embodiments, the status (e.g., pose; changes of pose) of the structure is communicated to an operator (e.g., medical professional; surgeon) of an insertion system (e.g., a manual insertion system; an automated or robotic insertion system) during implantation and/or retraction of the structure into and/or from the body portion in real-time while the operator is inserting and/or retracting the structure into and/or from the body portion so that the operator can act appropriately (e.g., to proceed with the implantation; to take corrective actions to avoid sub-optimal poses). For example, the at least one status reporting signal can be configured to be received by a status communication device (e.g., display device; screen; status indicator light; audio device; speaker; vibration motor) in operative communication with the at least one output interface 340, the status communication device configured to respond to the at least one status reporting signal by communicating a status signal (e.g., alarm; alert; message; information regarding the pose and/or changes of pose) indicative of the status (e.g., pose; changes of pose) of the structure to an operator of the system 300. In certain embodiments, the at least one status reporting signal is configured to be received by an automated insertion system (e.g., an actuator of an automated or robotic insertion system in operative communication with the at least one output interface 340 of the system 300 of FIG. 3) configured to respond automatically and in real-time to the at least one status reporting signal by manipulating the structure (e.g., to proceed with the implantation; to take corrective actions to avoid sub-optimal poses). In certain such embodiments, the at least one status reporting signal comprises at least one manipulation control signal.

Figure 10:
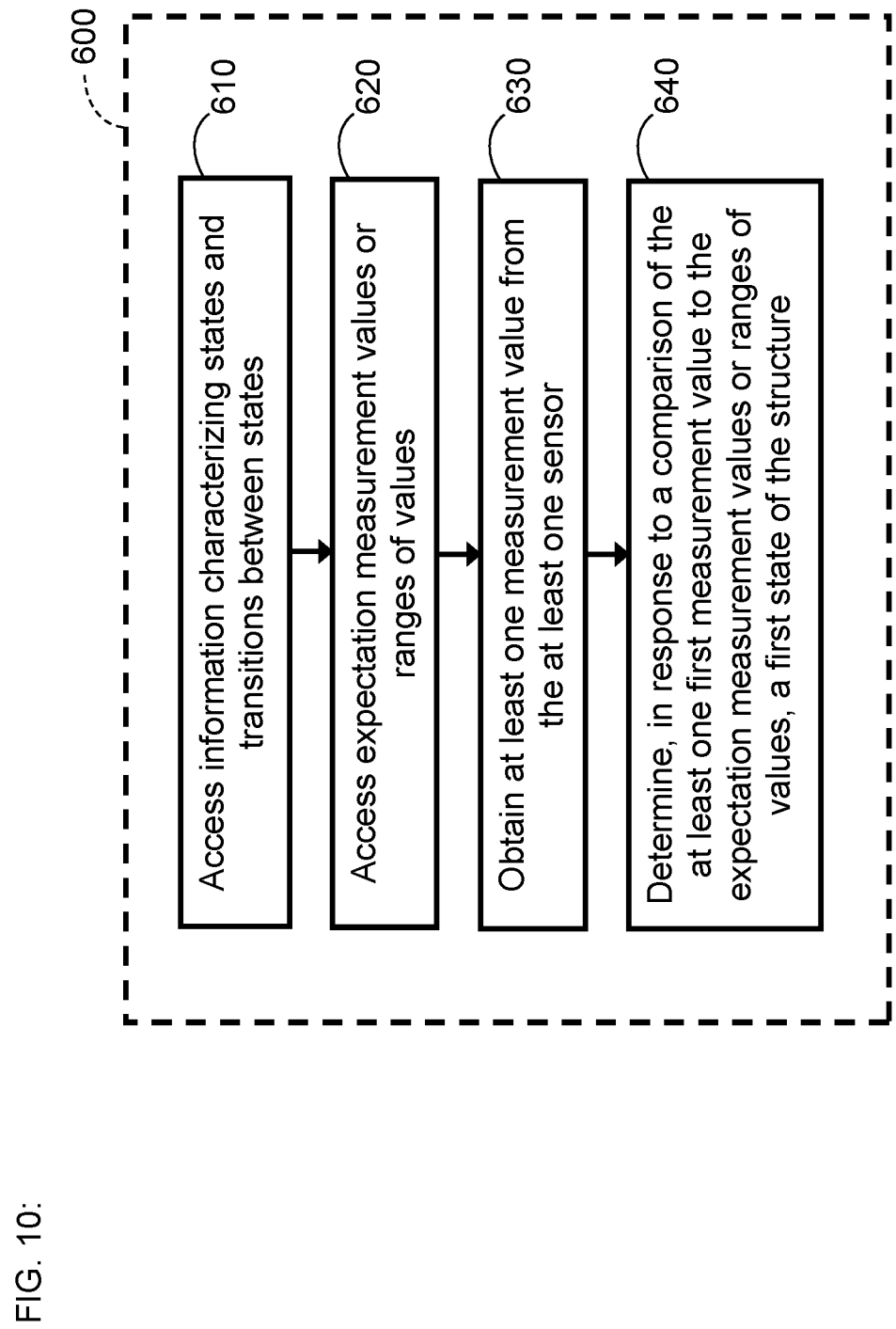
FIG. 10 is a flow diagram of an example method in accordance with certain embodiments described herein.

FIG. 10 is a flow diagram of an example method 600 in accordance with certain embodiments described herein. In an operational block 610, the method 600 comprises accessing information characterizing states and transitions between states of a structure at least partially inserted into a body portion of a recipient. In certain embodiments, accessing the expectation measurement values or ranges of values comprises calculating the expectation measurement values or ranges of values using a parameterized model (e.g., a probabilistic model or a canonical model of a parameterized description) of the structure and/or the body portion.

FIGS. 7A-7C show an example of such states and transitions between states for a structure comprising an electrode array 146 of a cochlear implant system 100, and the body portion comprising a cochlea 140 of the recipient. As shown in FIGS. 7A-7C, the states of the array 146 comprise at least (i) a folded state in which an end portion of the array 146 within the cochlea 140 is folded over, and (ii) an unfolded (e.g., modiolar-proximal) state in which the end portion 250 of the array 146 within the cochlea 140 is not folded over (e.g., and is not bent). In certain embodiments, the states of the array 146 further comprise a "bent" state (e.g., between the "folded" state and the "unfolded" state in which the end portion 250 of the array 146 within the cochlea 140 is bent (e.g., by more than a predetermined amount).

In an operational block 620, the method 600 further comprises accessing expectation measurement values or ranges of values expected to be generated by at least one sensor of the structure. For example, the at least one sensor can comprise at least one electrode 148 of the electrode array 146, which is responsive to the state (e.g., pose) of the array 146, and the expectation measurement values or ranges of values can correspond to measurements expected to be generated while the electrode array 146 is in each of the states (e.g., shown in FIGS. 7A-7C). As schematically illustrated by FIG. 9, the expectation measurement values can include measurement values that are expected to be generated by the at least one electrode 148 when the array 146 is in each of the states.

In an operational block 630, the method 600 further comprises obtaining at least one first measurement value from the at least one sensor at a corresponding time period. The at least one first measurement value can be selected from the group consisting of: transimpedance measurement (e.g., transimpedance gradient measurement); voltage measurement; impedance measurement; four-point impedance measurement; electrocochleography measurement; electrically evoked compound action potential (ECAP) measurement.

In an operational block 640, the method 600 further comprises determining, in response to a comparison of the at least one first measurement value to the expectation measurement values or ranges of values, a first state of the structure during the first time period. For example, referring to FIG. 9, the at least one first measurement value (denoted by the white cross labeled "new observations") can be compared to the expectation measurement values (denoted by the black circles). The state corresponding to the expectation measurement value most closely matching the at least one first measurement value can be considered to be the state of the structure during the time period.

In certain embodiments, the method 600 further comprises adjusting the expectation measurement values or ranges of values in response to the at least one first measurement value. For example, if a measurement (e.g., four-point impedance) is expected to provide a first expected value of 4 when in an unfolded state and a second expected value of 1 when in the folded state, and the first measurement value is 3 and the array 146 is assumed to be in the unfolded state, the expectation measurement values of the unfolded state and the folded state can be adjusted to be lower (e.g., 3.6 and 0.9, respectively) based on a pre-defined logic, so that the expectation measurement values reflect more closely the actual measurement values being generated by the electrodes 148. In this way, certain embodiments can be used to estimate and correct for bias in the measurement values provided by the electrodes 148.

In certain embodiments, the method 600 can be used to monitor the state (e.g., pose) in real-time during the implantation process. For example, the method 600 can further comprise obtaining at least one second measurement value from the at least one sensor at a second time period after the first time period and determining, in response to a comparison of the at least one second measurement value to the expectation measurement values or ranges of values, a second state of the structure during the second time period. The measurement values can be obtained from the at least one sensor continuously, at predetermined intervals, and/or in response to requests by the operator during the implantation process, and the comparison to the expectation measurement values or ranges of values can be made with sufficient speed to provide real-time feedback to the operator.

It is to be appreciated that the embodiments disclosed herein are not mutually exclusive and may be combined with one another in various arrangements. In addition, although the disclosed methods and apparatuses have largely been described in the context of conventional cochlear implants, various embodiments described herein can be incorporated in a variety of other suitable devices, methods, and contexts, including but not limited to totally implantable cochlear implants ("TICIs") and/or mostly implantable cochlear implants ("MICIs"). For example, TICIs can utilize a battery and a microphone which are both implanted within the body of the recipient (e.g., as components of either a monolithic system or as a collection of modules coupled together) that are capable of operating, at least for a period of time, without the need for an external device and without the need for any transcutaneous transmission of signals. For another example, MICIs can utilize a battery implanted within the body of the recipient, all or some of the sound processing can be performed by the implant, and a smaller (or very small) external processor can contain the microphone and the capability to wirelessly transmit information to the implant via RF signals (as done in current cochlear implant systems) or any other wireless data and/or audio transmission scheme.

More generally, as can be appreciated, while certain embodiments are described herein with reference to an illustrative medical device, namely a cochlear implant system, certain other embodiments can be used in a variety of other contexts. For example, certain embodiments described herein can be used in other implantable medical device devices that, while providing a wide range of therapeutic benefits to recipients, patients, or other users, may benefit from improved positioning of the medical device. For example, the systems and methods described herein can be used with other hearing prostheses, visual prostheses, sensors, stents and/or stentrodes inserted into arteries, pacemaker leads inserted into the chambers of the heart, drug delivery systems, defibrillators, functional electrical stimulation devices, catheters, or other context to monitor and to provide real-time feedback in procedures involving surgical interventions of elongate structures into unseen cavities. Other, non-medical context can include but are not limited to: underwater or otherwise inhospitable cabling (e.g., by an automated or robotic system), drill bores in exploratory mining (e.g., to map mineral deposits).

The invention described and claimed herein is not to be limited in scope by the specific example embodiments herein disclosed, since these embodiments are intended as illustrations, and not limitations, of several aspects of the invention. Any equivalent embodiments are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example embodiments disclosed herein, but should be defined only in accordance with the claims and their equivalents.

What is claimed is:

1. A method comprising:
    receiving, using at least one processor, first information regarding a pose of a structure in a first time period, the structure configured to be inserted into a body portion of a recipient, the first information comprising a first measurement set comprising one or more first measurement values, at least some of the one or more first measurement values generated using a plurality of sensors distributed along the structure, the one or more first measurement values indicative of the pose of the structure in the first time period;
    generating, in real-time and using the at least one processor, an estimate of the pose of the structure using at least the first information and a probabilistic model of the structure and/or the body portion, wherein said generating comprises:

estimating likelihoods of multiple different predicted poses by comparing the first measurement set to predicted value sets based on the probabilistic model for the multiple different predicted poses; and
setting the estimate of the pose of the structure as one of the predicted poses based on the likelihoods; and
manipulating the structure during implantation and/or retraction of the structure into and/or from the body portion in real-time based on the estimate of the pose of the structure.

2. The method of claim 1, wherein said generating the estimate of the pose of the structure comprises updating a previous estimate of the pose in response to the first measurement set.

3. The method of claim 1, wherein said generating the estimate of the pose comprises:
generating, in real-time and using the at least one processor, a first ensemble of potential poses of the structure, the first ensemble comprising the multiple different predicted poses and generated using the probabilistic model of the structure and/or the body portion; and
selecting, in real-time and using the at least one processor, the estimate of the pose from the multiple different predicted poses.

4. The method of claim 3, wherein said generating the first ensemble of potential poses further comprises generating, in real-time and using the at least one processor, expectations of measurement values corresponding to the multiple different predicted poses, the method further comprising:
receiving, using the at least one processor, a second measurement set comprising one or more second measurement values, at least some of the one or more second measurement values generated using the plurality of sensors, the one or more second measurement values indicative of the pose of the structure in a second time period; and
comparing, in real-time and using the at least one processor, the second measurement set to the expectations of the measurement values corresponding to the multiple different predicted poses.

5. The method of claim 3, wherein the second time period is after the first time period.

6. The method of claim 3, further comprising:
generating, in real-time and using the at least one processor, a second ensemble of potential poses of the structure in a third time period, the second ensemble generated using the probabilistic model; and
selecting, in real-time and using the at least one processor, another estimate of the pose from the second ensemble of potential poses.

7. The method of claim 6, wherein the third time period is after the second time period.

8. The method of claim 1, wherein the structure comprises an electrode array of a cochlear implant system, the plurality of sensors comprises a plurality of sensors on the electrode array, and the body portion comprises a cochlea of the recipient.

9. The method of claim 1, further comprising generating, in real-time and using the at least one processor, at least one status reporting signal, in response at least in part to the estimate and during insertion of the structure into the body portion and/or retraction of the structure from the body portion, the at least one status reporting signal configured to be received by at least one of:
a status communication device configured to respond to the at least one status reporting signal by communicating a status signal to a user of the status communication device, the status signal indicative of a status of the structure; and
an automated actuator configured to respond to the at least one status reporting signal by manipulating the structure.

10. The method of claim 1, further comprising communicating information regarding the estimate to an operator of an insertion system being used to insert the structure into the body portion and/or retract the structure from the body portion.

11. The method of claim 1, wherein:
the probabilistic model of the structure and/or the body portion comprises information characterizing states and transitions between states of the structure at least partially inserted into the body portion of the recipient; and
the first information further comprises expectation measurement values or ranges of values expected to be generated by the plurality of sensors.

12. The method of claim 11, wherein said generating the estimate comprises calculating the expectation measurement values or ranges of values using the probabilistic model of the structure and/or the body portion.

13. The method of claim 11, wherein the plurality of sensors is responsive to the states of the structure.

14. The method of claim 11, wherein the structure comprises an electrode array of a cochlear implant system, the plurality of sensors comprises at least one electrode of the electrode array, and the body portion comprises a cochlea of the recipient.

15. The method of claim 14, wherein the states of the structure comprise at least:
a folded state in which an end portion of the structure within the cochlea is folded over; and
an unfolded state in which the end portion of the structure within the cochlea is not folded over.

16. The method of claim 15, wherein the states of the structure further comprise a bent state in which the end portion of the structure within the cochlea is bent by more than a predetermined amount.

17. The method of claim 14, wherein the one or more first measurement values are selected from the group consisting of: a transimpedance measurement; an electrocochleography measurement; an impedance measurement; a four-point impedance measurement; an electrically evoked compound action potential (ECAP) measurement.

18. The method of claim 11, further comprising adjusting the expectation measurement values or ranges of values in response to the one or more first measurement values.

19. The method of claim 11, further comprising:
obtaining at least one second measurement value from the plurality of sensors at a second time period after the first time period; and
determining, in response to a comparison of the at least one second measurement value to the expectation measurement values or ranges of values, a second state of the structure during the second time period.

20. The method of claim 1, wherein the plurality of sensors comprises an array of stimulation elements configured to deliver stimulation to the body portion.

21. The method of claim 1, further comprising generating second information indicative of the estimate of the pose of the structure, wherein the second information comprises at least one signal communicated to an operator of an insertion system and said manipulating is performed by the operator of the insertion system.

22. The method of claim 1, further comprising generating second information indicative of the estimate of the pose of the structure, wherein the second information comprises at least one signal communicated to an automated or robotic insertion system and said manipulating is performed by the automated or robotic insertion system.

23. The method of claim 1, wherein said generating further comprises analyzing a probability distribution of the multiple different predicted poses, the estimate of the pose corresponding to a mean, median, mode, and/or center-of-mass of the probability distribution and/or an uncertainty of the probability distribution.

24. The method of claim 1, wherein said estimated likelihoods have an inverse relationship with error metrics of the predicted poses.

25. The method of claim 1, wherein said setting the estimate comprises setting the estimate to be a predicted pose having a highest likelihood of the predicted poses.

26. A non-transitory computer readable storage medium having stored thereon a computer program that instructs a computer system to provide real-time information regarding a structure by at least:
  receiving first information regarding a pose of the structure in a first time period, the structure configured to be inserted into a body portion of a recipient, the first information comprising a first measurement set comprising one or more first measurement values, at least some of the one or more first measurement values generated using a plurality of sensors distributed along the structure, the one or more first measurement values indicative of the pose of the structure in the first time period;
  generating, in real-time, an estimate of the pose of the structure using at least the first information and a probabilistic model of the structure and/or the body portion, wherein said generating comprises:
    estimating likelihoods of multiple different predicted poses by comparing the first measurement set to predicted value sets from the probabilistic model for the multiple different predicted poses; and
    setting the estimate of the pose of the structure as one of the predicted poses based on the likelihoods; and
  manipulating the structure during implantation and/or retraction of the structure into and/or from the body portion in real-time based on the estimate of the pose of the structure.

27. The non-transitory computer storage medium of claim 26, wherein the structure comprises a stimulation assembly of a cochlear implant system, the plurality of sensors comprises an electrode array of the stimulation assembly, and the body portion comprises a cochlea of the recipient.

28. The non-transitory computer storage medium of claim 27, further configured to instruct the computer system to generate, in real-time, a status signal indicative of the estimate to at least one of a medical professional and an automated insertion system while the stimulation assembly is being inserted into the cochlea and/or retracted from the cochlea by the at least one of the medical professional and the automated insertion system.

29. The non-transitory computer storage medium of claim 28, wherein the status signal comprises at least one of: an alarm; an alert; a message; information regarding the estimate.

30. The non-transitory computer storage medium claim 26, wherein said generating the estimate comprises using the probabilistic model to calculate a probability distribution for various possible poses and using the probability distribution to derive the estimate.

31. The non-transitory computer storage medium of claim 30, wherein the estimate corresponds to at least one of: a mean of the probability distribution, a median of the probability distribution, a mode of the probability distribution, a center-of-mass of the probability distribution, a standard deviation of the probability distribution, and an interquartile range of the probability distribution.

* * * * *